(12) United States Patent
Berme et al.

(10) Patent No.: US 9,414,784 B1
(45) Date of Patent: Aug. 16, 2016

(54) MOVEMENT ASSESSMENT APPARATUS AND A METHOD FOR PROVIDING BIOFEEDBACK USING THE SAME

(71) Applicant: Bertec Limited, Edinburgh (GB)

(72) Inventors: Necip Berme, Worthington, OH (US); Jan Jakub Ober, Columbus, OH (US)

(73) Assignee: Bertec Limited, Edinburgh (GB)

( * ) Notice: Subject to any disclaimer, the term of this patent is extended or adjusted under 35 U.S.C. 154(b) by 0 days.

(21) Appl. No.: 14/929,303

(22) Filed: Oct. 31, 2015

Related U.S. Application Data

(63) Continuation-in-part of application No. 14/318,631, filed on Jun. 28, 2014, now Pat. No. 9,173,596.

(51) Int. Cl.
*A61B 5/00* (2006.01)
*G06F 19/00* (2011.01)
(Continued)

(52) U.S. Cl.
CPC . *A61B 5/486* (2013.01); *A61B 5/01* (2013.01); *A61B 5/11* (2013.01); *A61B 5/1112* (2013.01); *A61B 5/14542* (2013.01); *A61B 5/6814* (2013.01); *A61B 5/6823* (2013.01); *A61B 5/6831* (2013.01); *A61B 5/7246* (2013.01); *A61B 5/7278* (2013.01); *A61B 5/742* (2013.01); *A61B 5/7405* (2013.01); *A61B 5/746* (2013.01);
(Continued)

(58) Field of Classification Search
CPC ............. A63B 24/0021; A63B 24/003; A63B 2220/836; A63B 2220/833; A63B 2071/0655; A61B 5/11–5/1118; A61B 5/72; A61B 5/7264; A61B 5/4023; G06F 19/34; G06F 19/345; G06F 19/3418
See application file for complete search history.

(56) References Cited

U.S. PATENT DOCUMENTS

| 5,368,042 A | 11/1994 | O'Neal et al. |
| 6,006,129 A | 12/1999 | Watson |

(Continued)

FOREIGN PATENT DOCUMENTS

| WO | 90/14792 A1 | 12/1990 |
| WO | 2005/021107 A1 | 3/2005 |

OTHER PUBLICATIONS

First office action on the merits (Non-Final Rejection) in U.S. Appl. No. 14/318,631 mailed on Oct. 14, 2014.
(Continued)

*Primary Examiner* — William Thomson
*Assistant Examiner* — Marie Archer
(74) *Attorney, Agent, or Firm* — The Law Office of Patrick F. O'Reilly III, LLC

(57) ABSTRACT

A movement assessment apparatus configured to provide biofeedback to a user regarding one or more movements executed by the user is disclosed herein. The movement assessment apparatus generally includes a sensing device comprising one or more sensors, a data processing device operatively coupled to the sensing device, and a sensory output device operatively coupled to the data processing device. The data processing device is configured to determine executed motion data of a body portion of the user and/or executed motion data of an object manipulated by the user using one or more signals from the one or more sensors, to compare the executed motion data or a modified form of the executed motion data to baseline motion data of a reference motion, and to determine how closely the executed motion data or the modified form of the executed motion data conforms to the baseline motion data of the reference motion.

18 Claims, 22 Drawing Sheets

(51) Int. Cl.
*A63B 24/00* (2006.01)
*A61B 5/11* (2006.01)
*A61B 5/145* (2006.01)
*A61B 5/01* (2006.01)

(52) U.S. Cl.
CPC ............ *A61B 5/7455* (2013.01); *A61B 5/7475* (2013.01); *A63B 24/0021* (2013.01); *G06F 19/34* (2013.01); *G06F 19/345* (2013.01); *G06F 19/3418* (2013.01); *A61B 2503/10* (2013.01); *A61B 2562/029* (2013.01); *A61B 2562/0219* (2013.01); *A61B 2562/0271* (2013.01); *A63B 2220/833* (2013.01); *A63B 2220/836* (2013.01)

(56) References Cited

U.S. PATENT DOCUMENTS

| | | | |
|---|---|---|---|
| 6,032,530 A | 3/2000 | Hock | |
| 6,038,488 A | 3/2000 | Barnes et al. | |
| 6,113,237 A | 9/2000 | Ober et al. | |
| 6,152,564 A | 11/2000 | Ober et al. | |
| 6,295,878 B1 | 10/2001 | Berme | |
| 6,354,155 B1 | 3/2002 | Berme | |
| 6,389,883 B1 | 5/2002 | Berme et al. | |
| 6,571,193 B1 | 5/2003 | Unuma et al. | |
| 6,836,744 B1 | 12/2004 | Asphahani et al. | |
| 6,936,016 B2 | 8/2005 | Berme et al. | |
| 7,602,301 B1 | 10/2009 | Stirling et al. | |
| 8,157,730 B2 | 4/2012 | LeBoeuf et al. | |
| 8,181,541 B2 | 5/2012 | Berme | |
| 8,315,822 B2 | 11/2012 | Berme et al. | |
| 8,315,823 B2 | 11/2012 | Berme et al. | |
| D689,388 S | 9/2013 | Berme | |
| D689,389 S | 9/2013 | Berme | |
| 8,543,540 B1 | 9/2013 | Wilson et al. | |
| 8,544,347 B1 | 10/2013 | Berme | |
| 8,643,669 B1 | 2/2014 | Wilson et al. | |
| 8,700,569 B1 | 4/2014 | Wilson et al. | |
| 8,704,855 B1 | 4/2014 | Berme et al. | |
| 8,764,532 B1 | 7/2014 | Berme | |
| 8,847,989 B1 | 9/2014 | Berme et al. | |
| D715,669 S | 10/2014 | Berme | |
| 8,902,249 B1 | 12/2014 | Wilson et al. | |
| 8,915,149 B1 | 12/2014 | Berme | |
| 8,944,932 B2 | 2/2015 | Sato et al. | |
| 9,032,817 B2 | 5/2015 | Berme et al. | |
| 9,043,278 B1 | 5/2015 | Wilson et al. | |
| 9,066,667 B1 | 6/2015 | Berme et al. | |
| 9,081,436 B1 | 7/2015 | Berme et al. | |
| 9,168,420 B1 | 10/2015 | Berme et al. | |
| 9,173,596 B1 | 11/2015 | Berme et al. | |
| 2002/0123386 A1* | 9/2002 | Perlmutter | A63B 24/0021 473/223 |
| 2003/0216656 A1 | 11/2003 | Berme et al. | |
| 2004/0172213 A1 | 9/2004 | Kainulainen | |
| 2005/0033200 A1 | 2/2005 | Soehren et al. | |
| 2006/0136173 A1 | 6/2006 | Case, Jr. et al. | |
| 2007/0250134 A1 | 10/2007 | Miesel et al. | |
| 2008/0061949 A1 | 3/2008 | Ferguson et al. | |
| 2008/0182724 A1 | 7/2008 | Guthrie | |
| 2008/0228110 A1 | 9/2008 | Berme | |
| 2008/0319353 A1 | 12/2008 | Howell et al. | |
| 2011/0087137 A1 | 4/2011 | Hanoun | |
| 2011/0166488 A1 | 7/2011 | Miyake | |
| 2011/0277562 A1 | 11/2011 | Berme | |
| 2012/0130202 A1 | 5/2012 | Jain | |
| 2012/0266648 A1 | 10/2012 | Berme et al. | |
| 2012/0271565 A1 | 10/2012 | Berme et al. | |
| 2013/0110009 A1 | 5/2013 | Salorio | |
| 2013/0130213 A1 | 5/2013 | Burbank et al. | |
| 2013/0162427 A1 | 6/2013 | Dibenedetto et al. | |
| 2013/0194066 A1 | 8/2013 | Rahman et al. | |
| 2013/0204411 A1 | 8/2013 | Clark et al. | |
| 2013/0218295 A1 | 8/2013 | Holgate | |
| 2013/0244211 A1 | 9/2013 | Dowling et al. | |
| 2014/0081182 A1 | 3/2014 | Klose et al. | |
| 2014/0114453 A1 | 4/2014 | Bentley | |
| 2014/0257538 A1 | 9/2014 | Rose et al. | |
| 2014/0342844 A1 | 11/2014 | Mooney | |
| 2015/0096387 A1 | 4/2015 | Berme et al. | |

OTHER PUBLICATIONS

Second office action on the merits (Final Rejection) in U.S. Appl. No. 14/318,631 mailed on Feb. 23, 2015.
Notice of Allowance in U.S. Appl. No. 14/318,631, mailed on Jul. 1, 2015.

\* cited by examiner

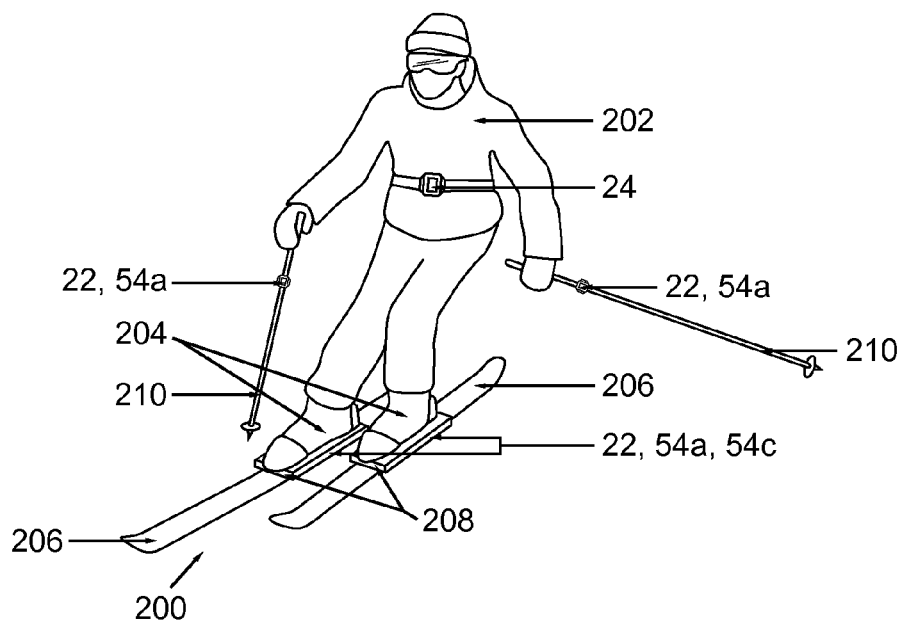
FIG. 20
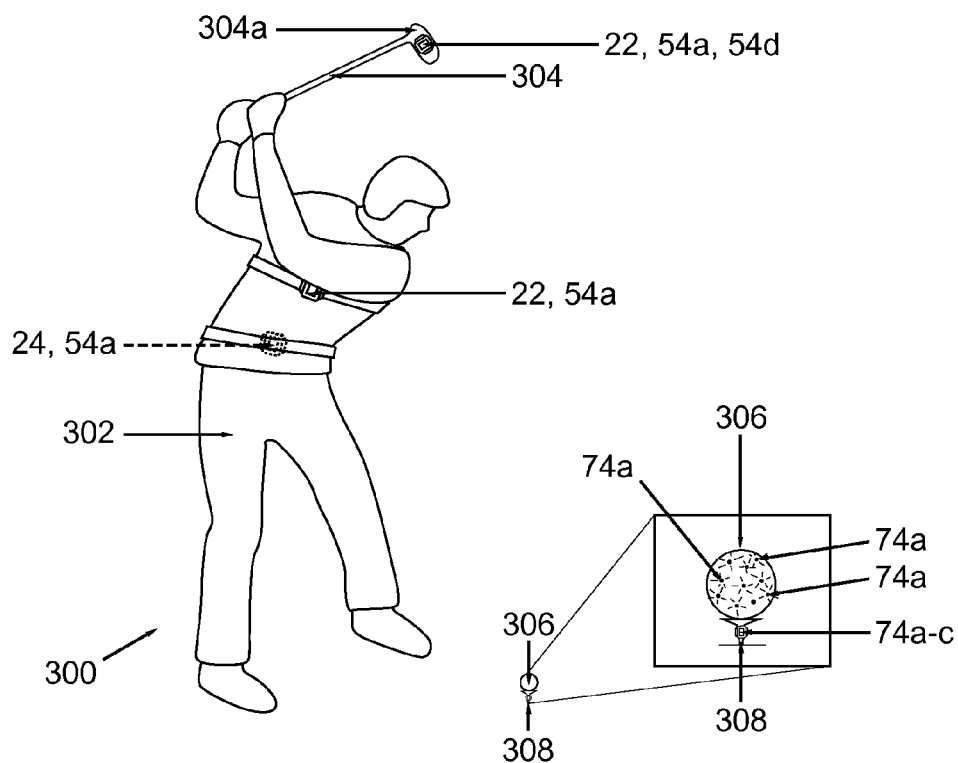
FIG. 21A         FIG. 21B

US 9,414,784 B1

MOVEMENT ASSESSMENT APPARATUS AND A METHOD FOR PROVIDING BIOFEEDBACK USING THE SAME

CROSS-REFERENCE TO RELATED APPLICATIONS

This is a continuation-in-part of U.S. Non-Provisional patent application Ser. No. 14/318,631, entitled "Movement Assessment Apparatus And A Method For Providing Biofeedback Using The Same", filed on Jun. 28, 2014, which is incorporated by reference herein in its entirety by this reference thereto.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a movement assessment apparatus. More particularly, the invention relates to a movement assessment apparatus configured to provide biofeedback to a user regarding one or more bodily movements executed by the user, and a method for providing biofeedback using the same.

2. Background

Training for a sporting activity or dance performance usually requires going through the same motion repeatedly. Typically, a coach or trainer first tells the trainee what to do, and then observes the motion and corrects mistakes. Particularly, in movements performed quickly, the coach explains the mistakes after the trainee performs the activity. This may take the form of showing a video of the trainee performing the activity, and then pointing out the errors. Seeing the mistakes after the fact is not as effective as getting instantaneous feedback while performing the activity. Still more effective is the feedback conveying not only at what point the mistake is made, but also letting the trainee know the magnitude of the error.

Therefore, what is needed is a movement assessment apparatus that is capable of providing biofeedback to a user regarding one or more bodily movements executed by the user. Moreover, what is needed is a method for providing biofeedback to a user regarding one or more bodily movements executed thereby that can be used to enhance the user's performance of a particular activity. Furthermore, a motion assessment apparatus is needed that can be effectively utilized during a plurality of different movement activities performed by a user, such as during the performance of various sports.

BRIEF SUMMARY OF EMBODIMENTS OF THE INVENTION

Accordingly, the present invention is directed to a movement assessment apparatus and method for providing biofeedback using the same that substantially obviates one or more problems resulting from the limitations and deficiencies of the related art.

In accordance with one or more embodiments of the present invention, there is provided a movement assessment apparatus configured to provide biofeedback to a user regarding one or more movements executed by the user. The movement assessment apparatus includes: at least one sensing device, the at least one sensing device comprising one or more sensors for detecting the motion of a body portion of a user and/or the motion of an object manipulated by the user and outputting one or more signals that are generated based upon the motion of the body portion of the user and/or the motion of the object, the at least one sensing device further comprising attachment means for attaching the at least one sensing device to the body portion of the user or to the object manipulated by the user; a data processing device operatively coupled to the at least one sensing device, the data processing device configured to receive the one or more signals that are output by the one or more sensors of the at least one sensing device, and to determine executed motion data of the body portion of the user and/or executed motion data of the object manipulated by the user using the one or more signals, the data processing device further configured to compare the executed motion data or a modified form of the executed motion data to baseline motion data of a reference motion, and to determine how closely the executed motion data or the modified form of the executed motion data conforms to the baseline motion data of the reference motion, the data processing device additionally configured to generate a sensory output signal based upon the comparison of the executed motion data or the modified form of the executed motion data to the baseline motion data of the reference motion; and a sensory output device operatively coupled to the data processing device, the sensory output device configured to generate a formed feedback signal for delivery to the user that is based upon the sensory output signal, the formed feedback signal comprising at least one of a visual indicator, an audible indicator, and a tactile indicator, and the sensory output device further configured to output the at least one of the visual indicator, the audible indicator, and the tactile indicator to the user in order to provide biofeedback as to conformity of the executed motion data to the baseline motion data of the reference motion.

In a further embodiment of the present invention, the one or more sensors of the at least one sensing device comprise at least one of: (i) an accelerometer, (ii) a gyroscope, and (iii) a magnetometer.

In yet a further embodiment, the at least one sensing device comprises a plurality of sensing devices, a first of the plurality of sensing devices configured to be attached to a limb of the user, a second of the plurality of sensing devices configured to be attached to a first torso location of the user, a third of the plurality of sensing devices configured to be attached to a head of the user, and a fourth of the plurality of sensing devices configured to be attached to a second torso location of the user.

In still a further embodiment, the attachment means of the at least one sensing device comprises a resilient band for attaching the at least one sensing device to one of a limb of the user, a torso of the user, a head of the user, and an object manipulated by the user.

In yet a further embodiment, the data processing device comprises a microprocessor.

In still a further embodiment, the at least one sensing device further comprises one or more additional sensors for detecting at least one of: (i) a position of the user, (ii) a body parameter of the user, and (iii) an environmental parameter.

In yet a further embodiment, the one or more additional sensors of the at least one sensing device comprise at least one of: (i) a global positioning system sensor for detecting a position of the user, (ii) a body oxygenation sensor for detecting an oxygen level or oxygen saturation level of the user, (iii) a body temperature sensor for detecting a body temperature of the user, (iv) an ambient temperature sensor for detecting a temperature of an environment in which the user is disposed, and (v) a humidity sensor for detecting a humidity level of the environment in which the user is disposed.

In still a further embodiment, the one or more sensors of the at least one sensing device are configured to detect the motion of an object manipulated by the user, and wherein the object manipulated by the user comprises one of: (i) a golf club, (ii) a baseball bat or softball bat, (iii) a tennis racket, (iv) an oar for rowing a boat, (v) a ski, (vi) a ski pole, and (vii) a handle bar of a handglider.

In accordance with one or more other embodiments of the present invention, there is provided a method for providing biofeedback to a user regarding one or more movements executed by the user. The method comprising the steps of: (i) providing a movement assessment apparatus configured to be worn by a user, the movement assessment apparatus including: at least one sensing device, the at least sensing device comprising one or more sensors for detecting the motion of a body portion of a user and/or the motion of an object manipulated by the user and outputting one or more signals that are generated based upon the motion of the body portion of the user and/or the motion of the object, the at least one sensing device further comprising attachment means for attaching the at least one sensing device to the body portion of the user or to the object manipulated by the user; a data processing device operatively coupled to the at least one sensing device, the data processing device configured to receive the one or more signals that are output by the one or more sensors of the at least one sensing device, and to determine executed motion data of the body portion of the user or executed motion data of the object manipulated by the user using the one or more signals, the data processing device further configured to compare the executed motion data or a modified form of the executed motion data to baseline motion data of a reference motion, and to determine how closely the executed motion data or the modified form of the executed motion data conforms to the baseline motion data of the reference motion, the data processing device additionally configured to generate a sensory output signal based upon the comparison of the executed motion data or the modified form of the executed motion data to the baseline motion data of the reference motion; and a sensory output device operatively coupled to the data processing device, the sensory output device configured to generate a formed feedback signal for delivery to the user that is based upon the sensory output signal, the formed feedback signal comprising at least one of a visual indicator, an audible indicator, and a tactile indicator, and the sensory output device further configured to output the at least one of the visual indicator, the audible indicator, and the tactile indicator to the user in order to provide biofeedback as to conformity of the executed motion data to the baseline motion data of the reference motion; (ii) outfitting a user or an object with the movement assessment apparatus, which includes attaching the attachment means of the at least one sensing device to a body portion of the user or to the object manipulated by the user; (iii) instructing the user to perform an activity where the user displaces at least one of the body portion of the user and/or the object manipulated by the user; (iv) detecting, by utilizing the at least one sensing device, the motion of the body portion of the user and/or the motion of the object manipulated by the user, and outputting one or more signals that are generated based upon the motion of the body portion of the user and/or the motion of the object manipulated by the user; (v) receiving, at the data processing device, the one or more signals that are output by the one or more sensors of the at least one sensing device; (vi) determining, by using the data processing device, executed motion data for an executed motion of the body portion of the user and/or for an executed motion of the object manipulated by the user using the one or more signals; (vii) comparing, by using the data processing device, the executed motion data or a modified form of the executed motion data to baseline motion data of a reference motion; (viii) determining, by using the data processing device, how closely the executed motion data or the modified form of the executed motion data conforms to the baseline motion data of the reference motion; (ix) generating, by using the data processing device, a sensory output signal based upon the comparison of the executed motion data or the modified form of the executed motion data to the baseline motion data of the reference motion; (x) generating, by using the sensory output device, a formed feedback signal for delivery to the user that is based upon the sensory output signal, the formed feedback signal comprising at least one of a visual indicator, an audible indicator, and a tactile indicator; and (xi) outputting the at least one of the visual indicator, the audible indicator, and the tactile indicator from the sensory output device to the user in order to provide quasi-instantaneous, real-time biofeedback as to conformity of the executed motion data to the baseline motion data of the reference motion.

In accordance with yet one or more other embodiments of the present invention, there is provided a movement assessment apparatus configured to provide biofeedback to a user regarding one or more movements executed by the user. The movement assessment apparatus includes: at least one sensing device, the at least one sensing device comprising one or more sensors for detecting the motion of a body portion of a user and/or the motion of an object manipulated by the user and outputting one or more signals that are generated based upon the motion of the body portion of the user and/or the motion of the object, the at least one sensing device further comprising attachment means for attaching the at least one sensing device to the body portion of the user or to the object manipulated by the user; at least one input device, the at least one input device configured to enable the user to manually select an activity from a plurality of activities, the selected activity having one or more reference motions associated therewith; a data processing device operatively coupled to the at least one sensing device and the at least one input device, the data processing device configured to receive the one or more signals that are output by the one or more sensors of the at least one sensing device, and to determine executed motion data of the body portion of the user and/or executed motion data of the object manipulated by the user using the one or more signals, the data processing device further configured to compare the executed motion data or a modified form of the executed motion data to baseline motion data of the one or more reference motions, and to determine how closely the executed motion data or the modified form of the executed motion data conforms to the baseline motion data of the one or more reference motions, the data processing device additionally configured to generate a sensory output signal based upon the comparison of the executed motion data or the modified form of the executed motion data to the baseline motion data of the one or more reference motions; and a sensory output device operatively coupled to the data processing device, the sensory output device configured to generate a formed feedback signal for delivery to the user that is based upon the sensory output signal, the formed feedback signal comprising at least one of a visual indicator, an audible indicator, and a tactile indicator, and the sensory output device further configured to output the at least one of the visual indicator, the audible indicator, and the tactile indicator to the user in order to provide biofeedback as to conformity of the executed motion data to the baseline motion data of the one or more reference motions.

In a further embodiment of the present invention, the at least one input device comprises a user interface disposed on a housing containing at least one of the at least one sensing device and the data processing device.

In yet a further embodiment, the user interface comprises at least one of: (i) one or more selection buttons or knobs, (ii) a keypad or keyboard, and (iii) a touchscreen-type visual display device.

In still a further embodiment, the at least one input device comprises a user interface disposed on the object, and wherein the object comprises a sports implement.

In yet a further embodiment, the sports implement comprises one of: (i) a golf club, (ii) a baseball bat or softball bat, (iii) a tennis racket, (iv) an oar for rowing a boat, (v) a ski, and (vi) a ski pole.

In still a further embodiment, the sensory output device comprises an audio headset configured to be worn on a head of the user, and wherein the audio headset is configured to generate the audible indicator that provides biofeedback as to the conformity of the executed motion data to the baseline motion data of the one or more reference motions.

In yet a further embodiment, the sensory output device comprises a light emitting device configured to be worn by the user, and wherein the light emitting device is configured to generate the visual indicator that provides biofeedback as to the conformity of the executed motion data to the baseline motion data of the one or more reference motions.

In still a further embodiment, the sensory output device comprises a vibratory device configured to be worn by the user, and wherein the vibratory device is configured to generate the tactile indicator that provides biofeedback as to the conformity of the executed motion data to the baseline motion data of the one or more reference motions.

In yet a further embodiment, the one or more sensors of the at least one sensing device are configured to detect the motion of an object manipulated by the user, and wherein the object manipulated by the user comprises one of: (i) a golf club, (ii) a baseball bat or softball bat, (iii) a tennis racket, (iv) an oar for rowing a boat, (v) a ski, (vi) a ski pole, and (vii) a handle bar of a handglider.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 20 is a diagrammatic perspective view of a second exemplary scenario wherein the movement assessment system described herein is being used to assess the athletic performance of a skier;

FIG. 21A is a diagrammatic perspective view of a third exemplary scenario wherein the movement assessment system described herein is being used to assess the athletic performance of a golfer;

FIG. 21B is an enlarged perspective view of the golf ball and tee in FIG. 21A, which further illustrates the details of the motion tracker reference sources on the golf ball and tee;

Throughout the figures, the same parts are always denoted using the same reference characters so that, as a general rule, they will only be described once.

DETAILED DESCRIPTION OF EMBODIMENTS OF THE INVENTION

Figures 1, 2:
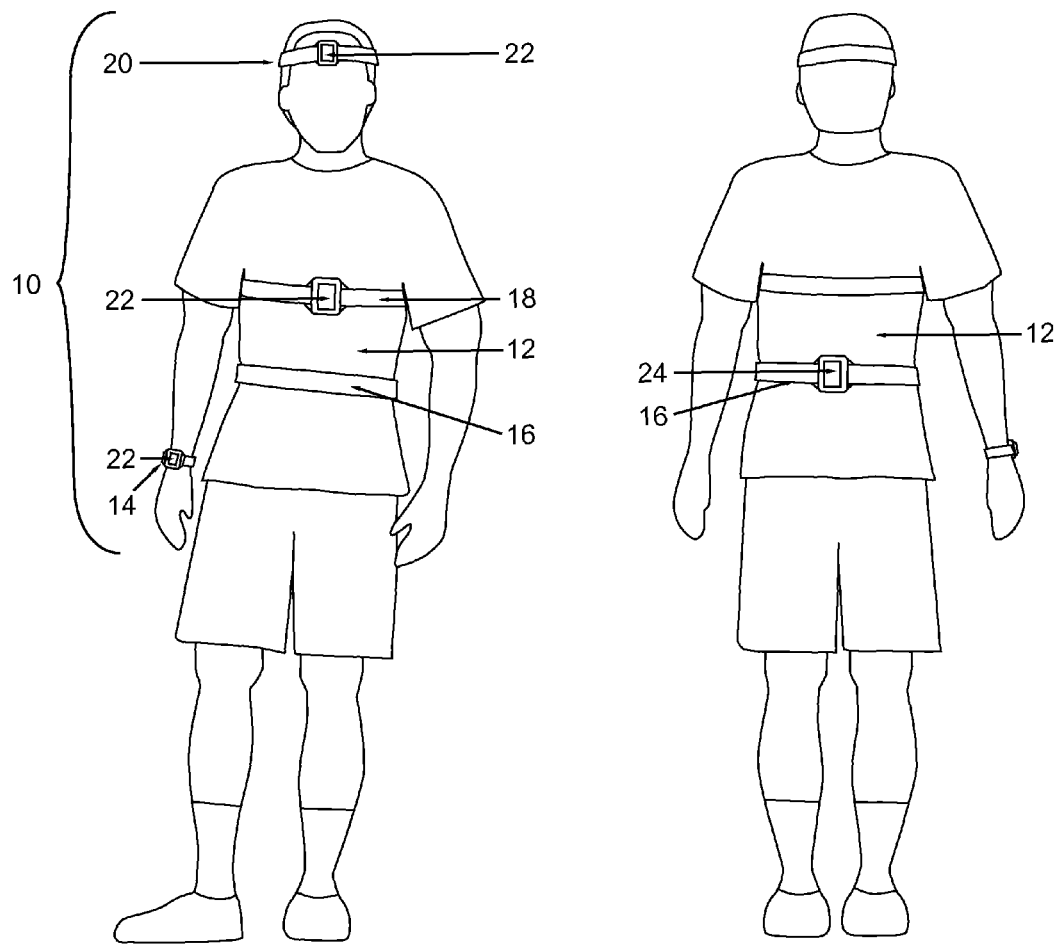
FIG. 1 is a diagrammatic front perspective view of a user or subject outfitted with a movement assessment system, according to one embodiment of the invention.
FIG. 2 is a diagrammatic rear perspective view of a user or subject outfitted with a movement assessment system, according to the embodiment of the invention in FIG. 1.

Initially, with reference to FIGS. 1 and 2, an illustrative embodiment of a movement assessment system 10 for providing biofeedback to a user 12 regarding one or more bodily movements executed by the user is shown. In FIG. 1, it can be seen that a user 12 may be outfitted with a plurality of different sensor band devices 14, 16, 18, 20 for detecting the motion of the user 12. In the illustrative embodiment, a user 12 is provided with a first sensor band device 14 on a wrist of his or her right arm, a second sensor band device 16 around his or her waist, a third sensor band device 18 around his or her chest, and a fourth sensor band device 20 around his or her head. In the illustrative embodiment, the second sensor band device 16 around the waist of the user 12 comprises a central control unit 24 (see FIG. 2), while the sensor band devices 14, 18, and 20 each comprise sensor units 22. In the illustrated embodiment, each of the sensor units 22 is operatively coupled to the central control unit 24 by wireless means, such as Bluetooth, or another suitable type of personal area network wireless means. However, in other embodiments, each of the sensor units 22 may be operatively coupled to the central control unit 24 by a wired connection.

Figure 11:
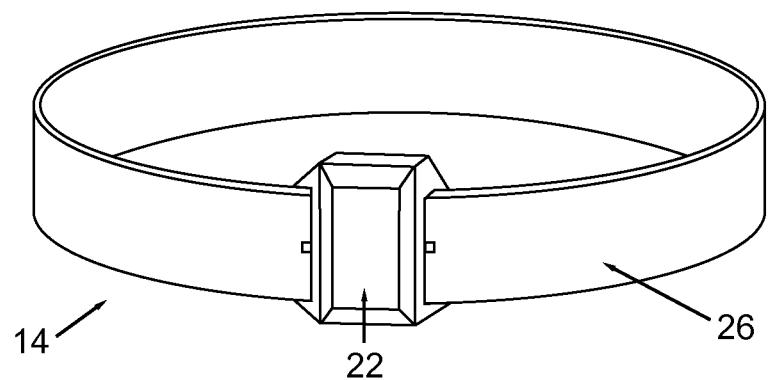
FIG. 11 is a diagrammatic perspective view of first exemplary attachment means for the sensor unit of the movement assessment system, according to one embodiment of the invention.

In the illustrated embodiment of FIGS. 1 and 2, each of the sensor units 22 is coupled to the respective body portion of the user 12 by a band. In FIG. 11, the first sensor band device 14, which attaches to the wrist of the user 12, is illustrated in more detail. As illustrated in this figure, the first sensor band device 14 generally comprises a sensor unit 22 attached to an elastic band 26. The band 26 is resilient so that it is capable of being stretched to accommodate the hand of the user 12, and then, fitted in place on the wrist of the user 12. The band 26 can be formed from any suitable stretchable fabric, such as neoprene, spandex, and elastane. Alternatively, the band 26 could be formed from a generally non-stretchable fabric, and be provided with latching means or clasp means for allowing the band 26 to be split into two portions (e.g., the band 26 could be provided with a snap-type latching device).

Figure 12:
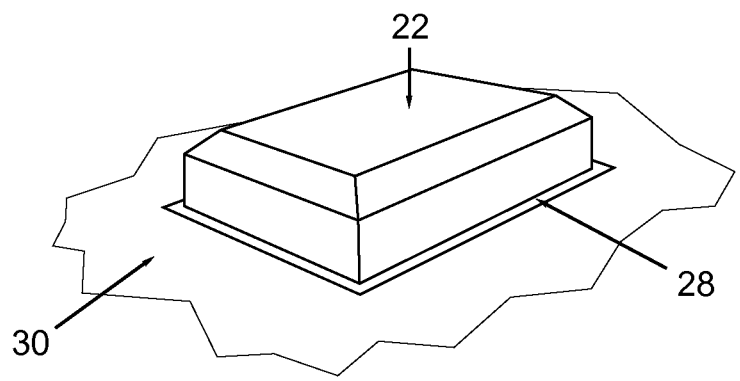
FIG. 12 is a diagrammatic perspective view of second exemplary attachment means for the sensor unit of the movement assessment system, according to another embodiment of the invention.
Figure 13:
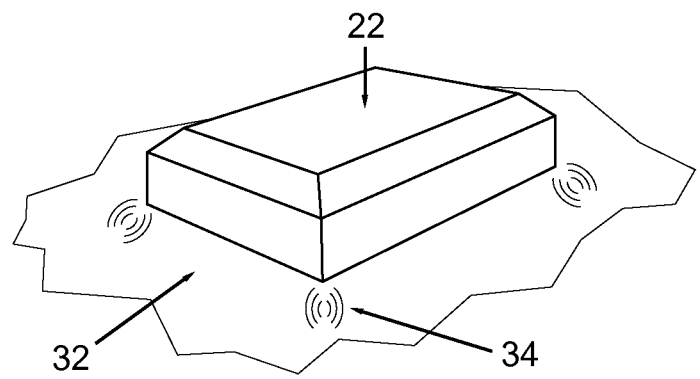
FIG. 13 is a diagrammatic perspective view of third exemplary attachment means for the sensor unit of the movement assessment system, according to yet another embodiment of the invention.

As illustrated in FIGS. 11-18, it is also possible to attach the sensor units 22 to the body portions of the user 12 using other suitable attachment means. For example, as shown in FIG. 12, the sensor unit 22 may be attached to a surface 30 (e.g., the skin or clothing item of the user 12 using adhesive backing means 28. The adhesive backing means 28 may comprise a removable backing member that is removed just prior to the sensor unit 22 being attached to a user 12 or object. Also, in some embodiments, the adhesive backing means 28 may comprise a form of double-sided bonding tape that is capable of securely attaching the sensor unit 22 to the user 22 or another object. As another example, referring to FIG. 13, the sensor unit 22 may be attached to a surface 32 (e.g., a metallic surface 32) using a magnetic attachment means (the magnetic flux lines 34 are shown in FIG. 13 to diagrammatically illustrate the magnetic attractive force between the magnetic attachment means of the sensor unit 22 and the metallic surface 32).

Figure 14:
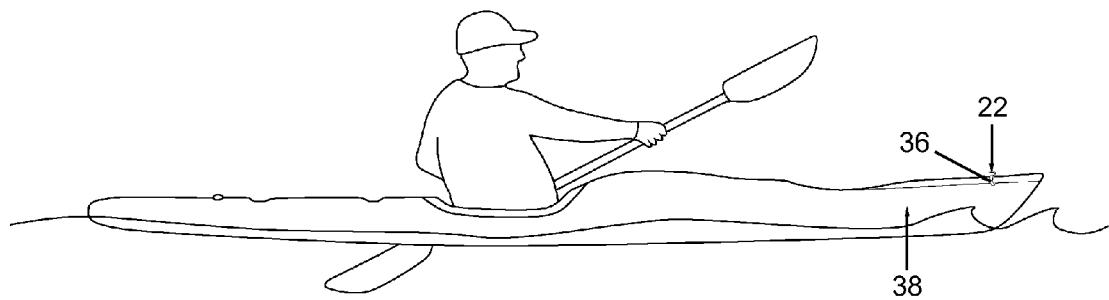
FIG. 14 is a diagrammatic perspective of a sensor unit of the movement assessment system attached to a boat using fourth exemplary attachment means, according to still another embodiment of the invention.
Figure 15:
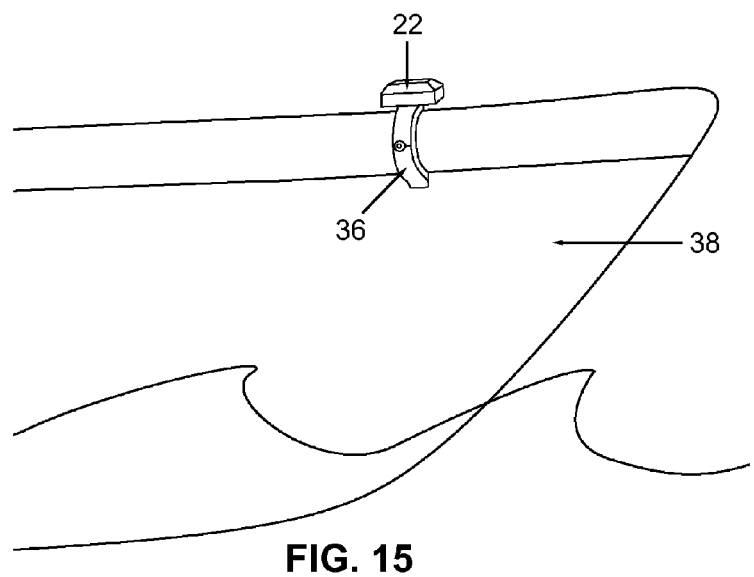
FIG. 15 is an enlarged perspective view of a portion of FIG. 14 illustrating in greater detail the manner in which the fourth exemplary attachment means of the sensor unit is coupled to the top rim of the boat.
Figure 16:
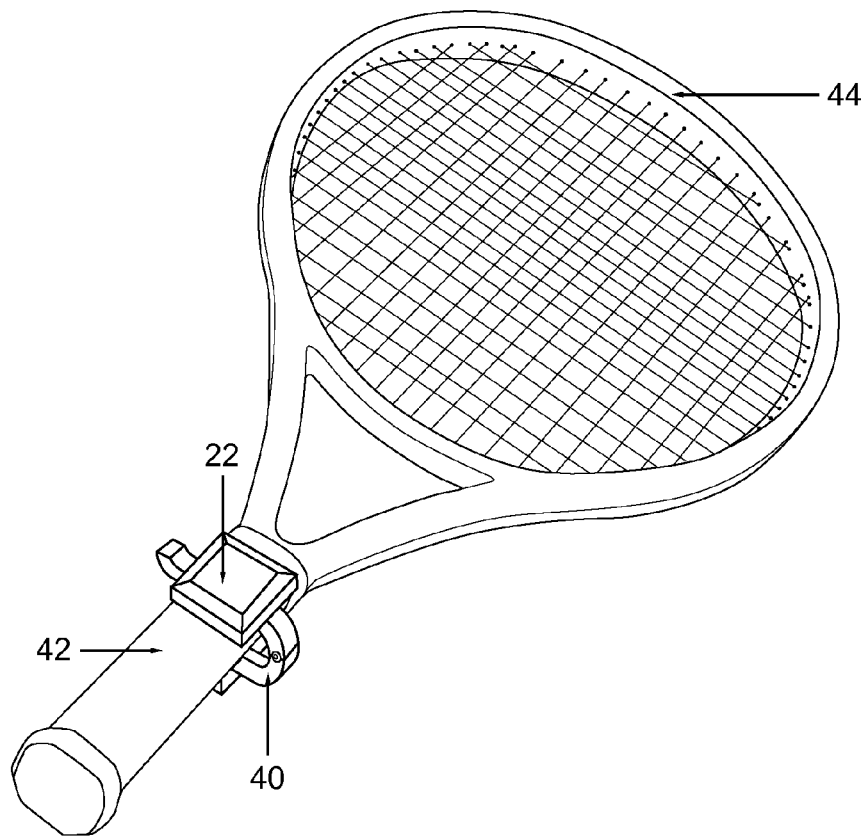
FIG. 16 is a diagrammatic perspective view of fifth exemplary attachment means for the sensor unit of the movement assessment system, according to yet another embodiment of the invention, wherein the fifth exemplary attachment means is used to attach the sensor unit to a handle of a tennis racket.
Figure 17:
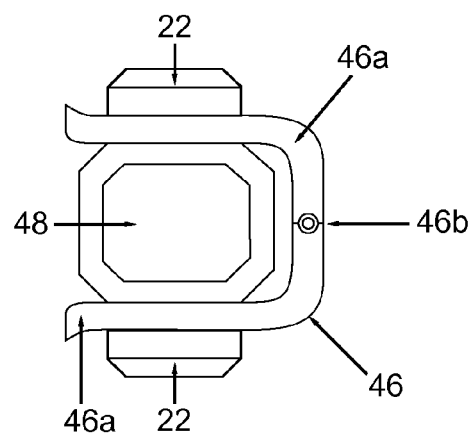
FIG. 17 is an end view illustrating in greater detail the manner in which the fifth exemplary attachment means is used to attach the sensor unit to the handle of the tennis racket.

In FIGS. 14-17, sensor units 22 attached by various clamping devices 36, 40, 46 are illustrated. In FIGS. 14 and 15, the sensor unit 22 is attached to the edge of a hull 38 of a boat, such as a rowboat, canoe, or kayak, by a C-shaped clamping device 36. Turning to FIGS. 16 and 17, it can be seen that two sensor units 22 are attached to opposed sides of a handle 42 of a tennis racket 44 by a clamping device 40. FIG. 17 illustrates an end view of a sensor unit 22 attached to a tennis racket handle 42 with handle end 48 by a hinged C-clamp device 46. Similarly, the C-clamp device 46 may be used to attach sensor unit 22 to other elongate objects, such as the shaft of a golf club. As shown in FIG. 17, the clamping portions 46a of the C-clamp device 46 pivot about a hinge portion 46b.

Figure 18:
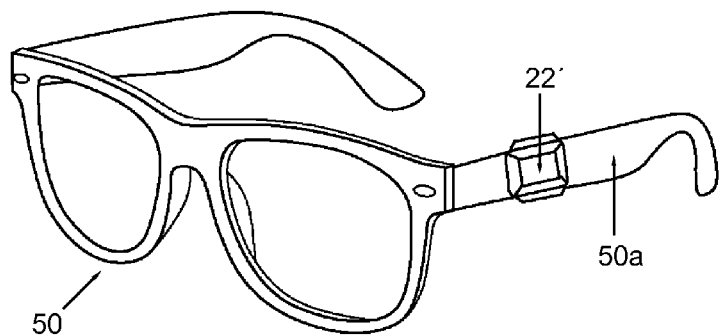
FIG. 18 is a diagrammatic perspective view of the sensor unit of the movement assessment system attached to an eyeglass frame, according to yet another embodiment of the invention.

Another mounting arrangement for a sensor unit 22' is shown in FIG. 18. In this figure, the sensor unit 22' is mounted to an eyeglass frame 50. In particular, the sensor unit 22' is attached to the temple portion 50a of the eyeglass frame 50. The sensor unit 22' is preferably more compact, and smaller in size, than the sensor unit 22 so that it can be easily attached to the eyeglass frame 50 without resulting in the deformation of the eyeglass frame 50 due to excessive weight applied thereto.

Hereafter, exemplary embodiments of the present invention will described with reference to block diagrams that diagrammatically illustrate the architecture of various components of the movement assessment system 10. With respect to these diagrammatic illustrations, it is to be understood that the connecting lines shown in the block diagram(s) included herein are intended to represent functional relationships and/or operational couplings between the various components. The compound conjunction "and/or" is used throughout this disclosure to mean one or the other, or both. For example, when a data processing device is said to be configured to determine a movement path and/or velocity profile, this is equivalent to stating that the data processing device is configured to determine a movement path, a velocity profile, or both a movement path and a velocity profile.

Figure 3:
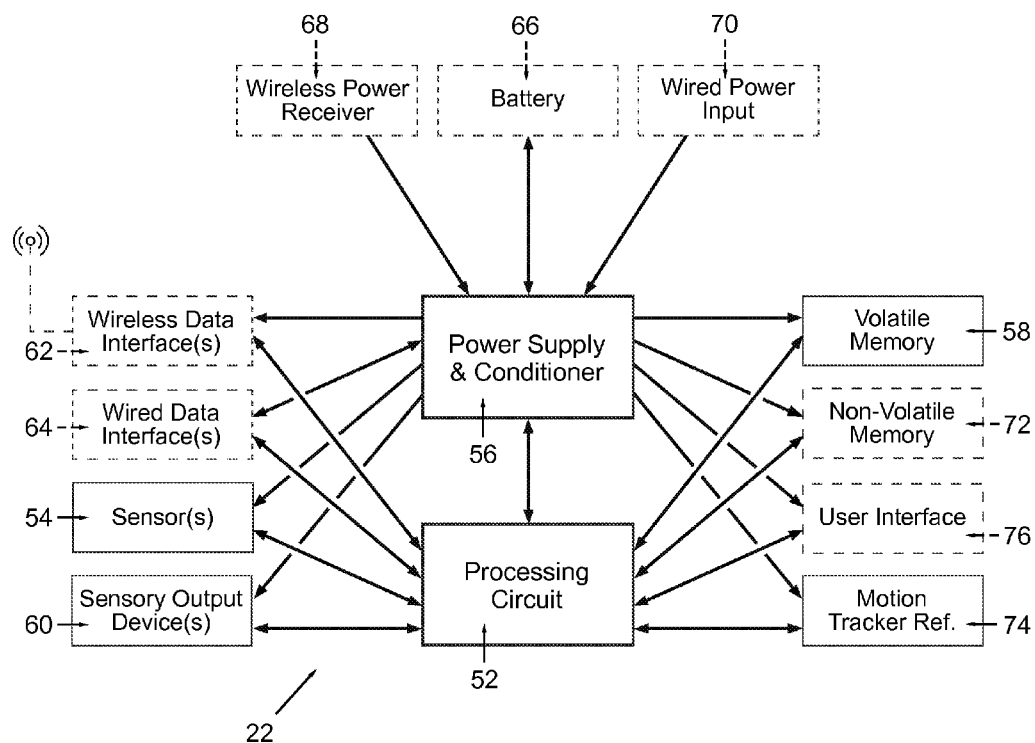
FIG. 3 is a schematic block diagram of pertinent electrical components of an illustrative sensor unit of the movement assessment system, according to an embodiment of the invention.

Now, with reference to FIG. 3, an exemplary sensor unit 22 that may be utilized in conjunction with the embodiments described herein will be described in detail. As shown in FIG. 3, the sensor unit 22 generally comprises a processing circuit 52, one or more sensors 54 that are operatively coupled to the processing circuit 52, volatile memory 58 operatively coupled to the processing circuit 52 for storing data during the processing thereof, and a power supply and conditioner 56 operatively coupled to each of the electrical components 52, 54, 58. The processing circuit 52 may comprise a microprocessor or other suitable processing means. The power supply and conditioner 56 regulates the power that is delivered to the electrical components 52, 54, 58 by modifying the level and characteristics thereof (e.g., by regulating the voltage delivered from the power supply 66, 68, 70 by adjusting the voltage level and characteristics in accordance with the specific needs of the electrical components 52, 54, 58). Referring again to FIG. 3, it can be seen that the power supply or power source for the sensor unit 22 may be in the form of a battery 66 disposed within the sensor unit 22 itself, a wireless power receiver 68 operatively coupled to a remote wireless power transmitter, and/or a wired power input 70 (e.g., an electrical wire or wires connecting the sensor unit 22 to the power supply in the central control unit 24). As shown in FIG. 3, no matter which one or combination of the power supplies 66, 68, 70 is used in the sensor unit 22, the power supplies 66, 68, 70 are all operatively connected to the power supply and conditioner 56 so that the power delivered thereby can be conditioned prior to being transmitted to the electrical loads (e.g., electrical components 52, 54, 58) in the sensor unit 22. If a wireless power receiver 68 is utilized as the power supply for the sensor unit 22, a wireless power transmitter 80' may be located in the central control unit 24 of the movement assessment system 10. Also, in addition to volatile memory 58, the sensor unit 22 also may have non-volatile memory 72 in the form of a data storage device, such as one or more compact hard drives, flash drives, memory cards, memory sticks, or any combination thereof.

Figure 5:
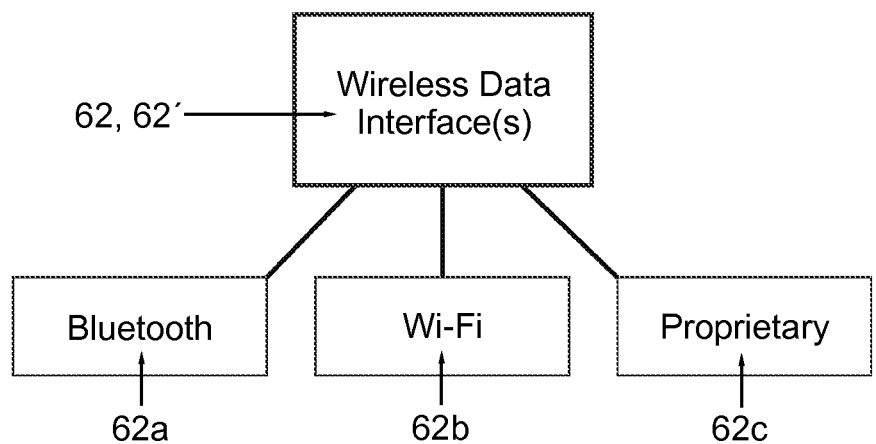
FIG. 5 illustrates various forms in which wireless data interface(s) of the exemplary movement assessment system may be embodied, according to an embodiment of the invention.

Also, as shown in FIG. 3, the sensor unit 22 may comprise one or more wireless data interfaces 62 for electrically coupling the sensor unit 22 to other devices, such as a central control unit 24. In particular, with reference to FIG. 5, the one or more wireless data interfaces 62 may comprise a Bluetooth device 62a for operating as part of a personal area network ("PAN"), a Wi-Fi device 62b for operating as part of a wireless local area network ("WLAN"), and/or a proprietary wireless interface device 62c that utilizes a proprietary communications protocol. It is to be understood that the sensor unit 22 may comprise one, two, or all three of these data interface devices 62a, 62b, 62c depending on the needs of the particular movement assessment system 10 in which they are being utilized.

Figure 6:
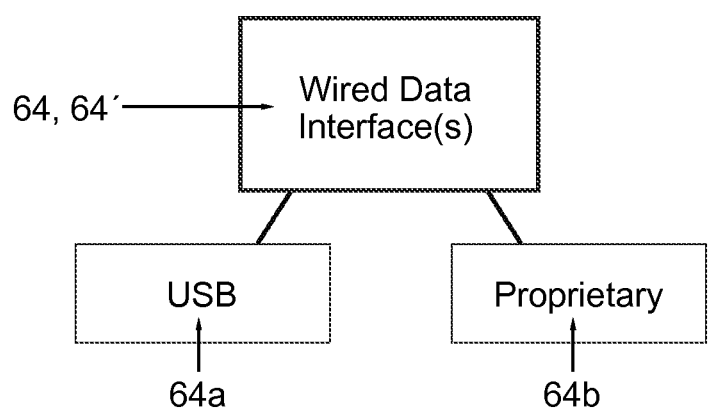
FIG. 6 illustrates various forms in which wired data interface(s) of the exemplary movement assessment system may be embodied, according to an embodiment of the invention.

Referring again to FIG. 3, the sensor unit 22 also may comprise one or more wired data interfaces 64 for electrically coupling the sensor unit 22 to other devices, such as a central control unit 24, by hard wiring (e.g., an electrical wire or cable). Specifically, with reference to FIG. 6, the one or more wired data interfaces 64 may comprise a universal serial bus ("USB") port 64a for accommodating a USB cable between devices (e.g., between devices 22, 24) and/or a proprietary data port 64b for accommodating a proprietary cable between devices (e.g., between devices 22, 24). It is to be understood that the sensor unit 22 may comprise one or both of these wired data interfaces 64 depending on the needs of the particular movement assessment system 10 in which they are being employed.

Figure 7:
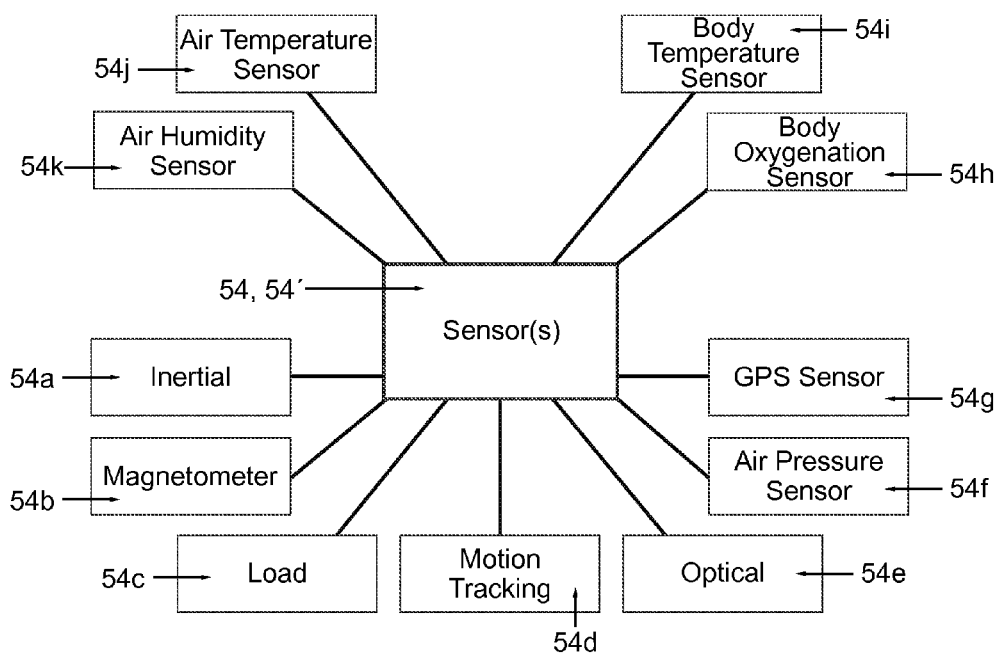
FIG. 7 illustrates various forms in which sensor(s) of the exemplary movement assessment system may be embodied, according to an embodiment of the invention.

As described above in conjunction with FIG. 3, the sensor unit 22 comprises one or sensors 54 for sensing one or more measurable quantities associated with a subject or user (e.g., an athlete) or an object (e.g., a boat, a golf ball, a handglider, etc.). With reference to FIG. 7, the one or more sensors 54 in the sensor unit 22 may comprise an inertial sensor 54a for measuring motion, a magnetometer-type sensor 54b for measuring the orientation of the user or object relative to the Earth's magnetic field, a load sensor 54c for measuring the force and/or moments exerted on a particular user or object, a motion tracking sensor 54d for measuring the motion of a user or object, an optical sensor 54e for measuring the motion of a user or object using a reference light source, an air pressure sensor 54f for measuring the ambient air pressure or pressure inside a particular enclosure, a global positioning system ("GPS") sensor 54g for measuring the location or position of a user or object anywhere on or near the Earth using satellite technology, a body oxygenation sensor 54h for detecting an oxygen level or oxygen saturation level of a subject or user (e.g., athlete), a body temperature sensor 54i for detecting a body temperature of the user, an ambient temperature sensor 54j for detecting a temperature of an indoor or outdoor environment in which the user is disposed, and/or a humidity sensor 54k for detecting a humidity level of the indoor or outdoor environment in which the user is disposed. It is to be understood that the sensor unit 22 may comprise any number or all of these sensors 54a, 54b, 54c, 54d, 54e, 54f, 54g, 54h, 54i, 54j, 54k depending on the needs of the particular movement assessment system 10 in which they are being employed.

In one or more further embodiments, the one or more inertial sensors 54a for measuring motion may comprise one or more of the following: (i) an accelerometer, (ii) a gyroscope, (iii) a magnetometer, and (iv) a geomagnetic sensor. Also, the one or more inertial sensors 54a may include a plurality of each of the following sensor types in order to measure motion in multiple directions (e.g., three accelerometers to measure acceleration in three (3) dimensional space). The data processing device (e.g., the processing circuit 52', which may include a microprocessor) of the central control unit 24 and/or the data processing device (e.g., the processing circuit 52, which may include a microprocessor) of the sensor unit 22 may utilize the output signals of the one or more inertial sensors 54a to determine a movement path and/or velocity profile of the body portion of the user while he or she is performing a particular activity (i.e., the data processing device may determine a movement path, a velocity profile, or both a movement path and a velocity profile of the body portion of the user). The data processing device (e.g., the processing circuit 52', which may include a microprocessor) of the central control unit 24 and/or the data processing device (e.g., the processing circuit 52, which may include a microprocessor) of the sensor unit 22 is further configured to compare the movement path and/or the velocity profile determined for the body portion of the user to a respective baseline movement path and/or velocity profile (i.e., the data processing device may compare a movement path, a velocity profile, or both a movement path and a velocity profile of the body portion of the user to a respective baseline movement path or baseline velocity profile). The data processing device (e.g., the processing circuit 52', which may include a microprocessor) of the central control unit 24 and/or the data processing device (e.g., the processing circuit 52, which may include a microprocessor) of the sensor unit 22 is further configured to determine how closely the movement path and/or the velocity profile determined for the body portion of the user conforms to the respective baseline movement path and/or baseline velocity profile (i.e., the data processing device may determine how closely a movement path, a velocity profile, or both a movement path and a velocity profile of the body portion of the user conforms to the respective baseline movement path or baseline velocity profile). Finally, the data processing device (e.g., the processing circuit 52', which may include a microprocessor) of the central control unit 24 and/or the data processing device (e.g., the processing circuit 52, which may include a microprocessor) of the sensor unit 22 is configured to generate a sensory output signal based upon the conformity of the movement path and/or the velocity profile of the user to the respective baseline movement path and/or baseline velocity profile.

Also, in one or more further embodiments, the global positioning system ("GPS") sensor 54g may be used to track the location of the activity that the user is performing. For example, if the user is a golfer, the global positioning system ("GPS") sensor 54g may be used to determine the location of the golf course that the golfer is playing. That way, the user is not required to manually track the location of each of his or her activities, thereby streamlining the assessment of his or her performance.

In addition, in one or more further embodiments, the body parameters of the user and environmental conditions may be sensed by the sensors 54, 54'. For example, the temperature and humidity of the environment (e.g., outdoor or indoor environment) in which the user is performing the activity may be sensed by air temperature sensor 54j and the humidity sensor 54k, respectively, while the air pressure of the environment may be sensed by the air pressure sensor 54f. For example, if the user is a golfer, the environmental sensors 54j, 54k, and 54f may be used to assess the weather conditions that the golfer is experiencing during his or her round of golf. Of course, if the weather conditions are adverse, this could significantly affect the performance of the golfer during his or her round of golf. Advantageously, the inclusion of the environmental sensors 54j, 54k, and 54f allow the movement and performance assessment apparatus and system to automatically track the performance of the user based upon specific weather conditions. The body parameters of the user who is executing the activity may also by correlated with his or her performance. For example, the body oxygenation sensor 54h and the body temperature sensor 54i may be used to monitor the physiological state of the user while he or she is performing the activity being monitored. Based upon the physiological parameters measured by the sensors 54h, 54i, the movement and performance assessment system may advantageously help a user determine if his or her performance is being adversely affected by his or her uncomfortable physiological state. For example, if the body temperature sensor 54i indicates that the user is too cold or too hot, the movement and performance assessment system could output this result to the user so that a user's unsatisfactory performance of a particular activity could be correlated with the abnormal body temperature.

Figure 8:
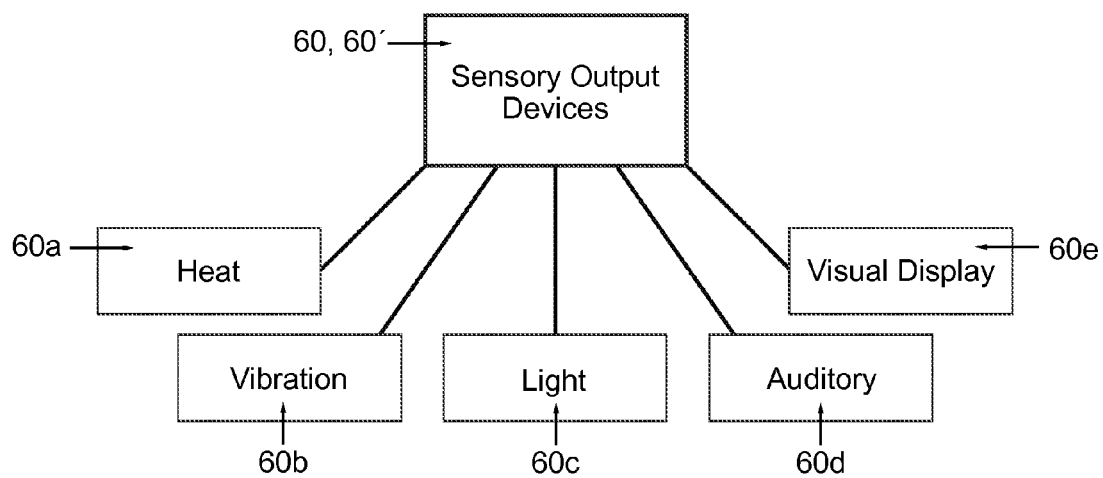
FIG. 8 illustrates various forms in which sensory output device(s) of the exemplary movement assessment system may be embodied, according to an embodiment of the invention.

Next, with reference once again to FIG. 3, the sensor unit 22 also may comprise one or more sensory output devices 60 for providing sensory stimuli to a subject or user so as to enable the movement assessment system 10 to provide the subject or user with biofeedback regarding his or her movement. In particular, with reference to FIG. 8, the one or more sensory output devices 60 may comprise a thermal or heat-based sensor output device 60a for delivering heat to the skin of a subject or user (i.e., a first type of tactile sensor output device), a vibratory sensory output device 60b for delivering vibrations to the limb or torso of a subject (i.e., a second type of tactile sensor output device), a light-emitting sensor output device 60c for providing a visual cue to a subject or user, an auditory sensory output device 60d for delivering an audible cue to the subject or user, and/or a visual display sensor output device 60e for providing a visual cue to a subject or user using a output display device. It is to be understood that the sensor unit 22 may comprise any number or all of these sensory output devices 60a, 60b, 60c, 60d, 60e depending on the needs of the particular movement assessment system 10 in which they are being employed.

In one or more embodiments, the auditory sensory output device 60d may comprise an audio headset that generates an audible cue in the form of a pleasant sound when the movement path and/or velocity profile of the user substantially conforms to the respective baseline movement path and/or baseline velocity profile (e.g., a sound with a frequency spectrum that lies within a comfortable range for the user, such as 2,000 Hertz or lower, or a sound having a comfortable decibel level for the user). In contrast, when the movement path and/or velocity profile of the user does not generally conform to the respective baseline movement path and/or baseline velocity profile, the audio headset generates an audible cue in the form of a unpleasant sound (e.g., a sound with a frequency spectrum that lies within an uncomfortable range for the user, such as between 2,000 Hertz and 4,000 Hertz, or a sound having a uncomfortable decibel level for the user, such as a sound over 100 decibels). In one or more other embodiments, the audible cue or sound generated by the audio headset becomes increasingly more unpleasant to the user as the movement path and/or velocity profile of the user deviates to a greater degree from the respective baseline movement path and/or baseline velocity profile (e.g., the decibel level of the sound gradually increases or the frequency level increases from a comfortable range to an uncomfortable range).

Figure 9:
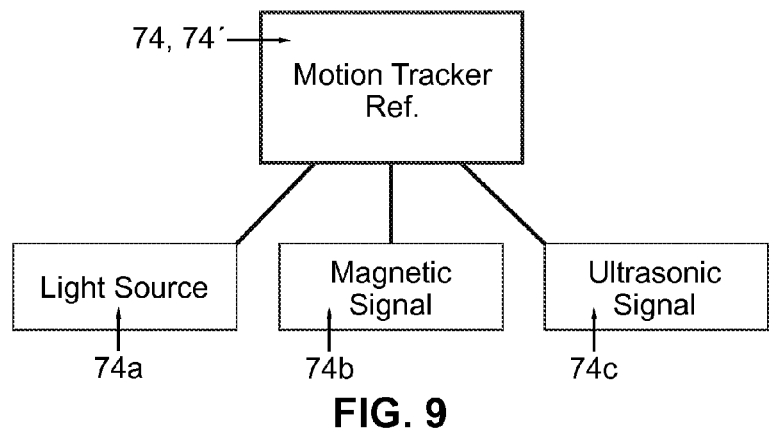
FIG. 9 illustrates various forms in which motion tracker reference source(s) of the exemplary movement assessment system may be embodied, according to an embodiment of the invention.

Referring again to FIG. 3, the sensor unit 22 also may comprise one or more motion tracker reference sources 74 for providing a point or frame of reference for any motion tracking sensors 54d that are used in conjunction with the movement assessment system 10. Specifically, as shown in FIG. 9, the one or more motion tracker reference sources 74 may comprise a motion tracker reference light source 74a for emitting light therefrom, a motion tracker reference magnetic signal 74b for generating a magnetic force and/or creating a magnetic field, and/or a motion tracker reference ultrasonic signal 74c for emitting an ultrasonic signal therefrom. It is to be understood that the sensor unit 22 may comprise one, two, or all three of these motion tracker reference sources 74a, 74b, 74c depending on the needs of the particular movement assessment system 10 in which they are being employed.

Figure 10:
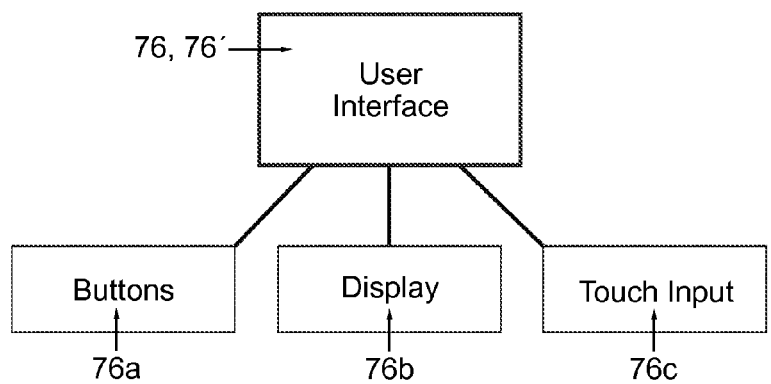
FIG. 10 illustrates various forms in which a user interface of the exemplary movement assessment system may be embodied, according to an embodiment of the invention.

Turning again to FIG. 3, the sensor unit 22 also may comprise a user interface 76 for allowing the subject or user to interact with the sensor unit 22 by controlling the settings thereof, etc. In particular, as shown in FIG. 10, the user interface 76 may comprise one or more buttons 76a that can be pressed by a user thereof or one or more knobs that can be rotated by a user thereof, a display 76b (i.e., visual display) that allows the user to view, for example, settings that can be adjusted on the sensor unit 22, and/or a touch input 76c that enables a user to interact with the sensor unit 22 by inputting commands directly on the display (e.g., the touch input 76c allows the user to make selections and change settings directly on the screen of the sensor unit 22). It is to be understood that the user interface 76 of the sensor unit 22 may comprise one, two, or all three of these means of input 76a, 76b, 76c depending on the needs of the particular movement assessment system 10 in which they are being employed. In addition to, or as an alternative to, the aforedescribed input devices, the user interface 76 of the sensor unit 22 may comprise a keypad or a keyboard that allows the user to make selections or input data into the sensor unit 22. When a touch-input 76c is provided, the keypad or a keyboard may be in the form of a graphic-based keypad or graphic-based keyboard that is displayed to the user on the touch-input 76c. Also, when the touch-input 76c is provided, the touch-input 76c may comprise one or more graphic-based selection buttons or knobs that enable the user to make various mode selections for the movement assessment system (i.e., to select a particular activity for analysis and/or to select particular aspects of a certain activity for analysis).

Figure 4:
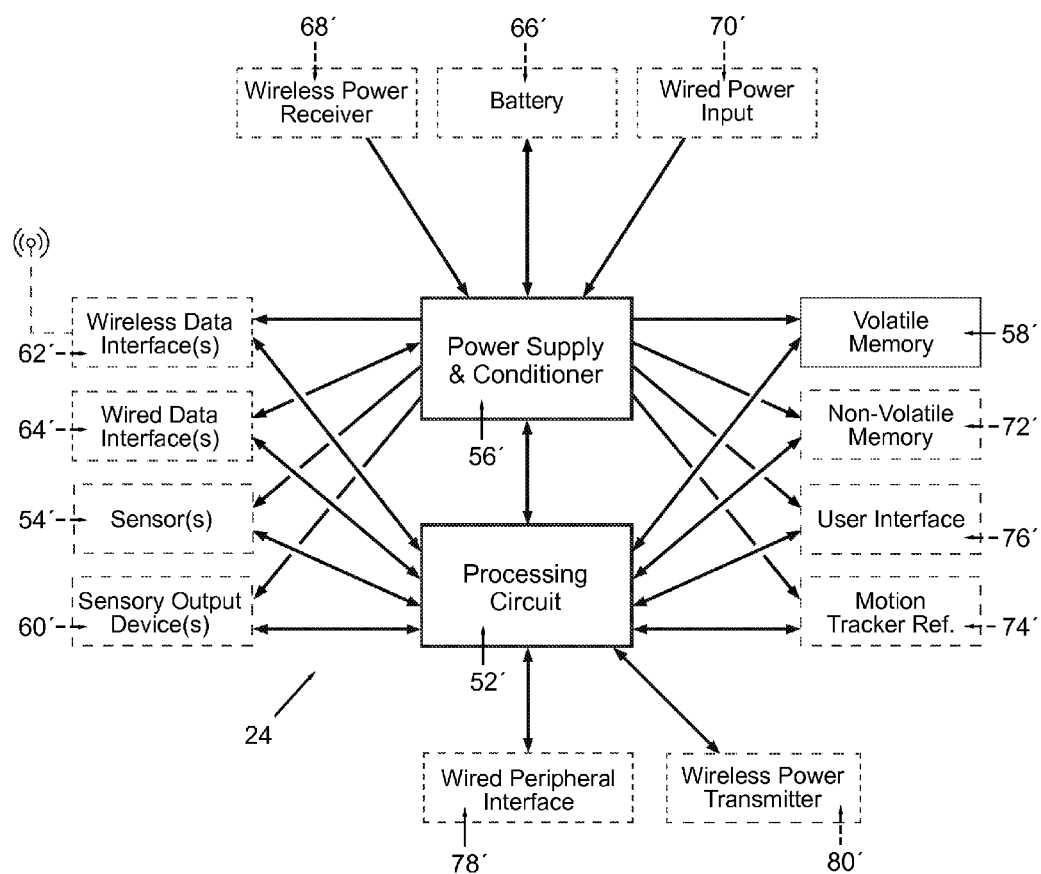
FIG. 4 is a schematic block diagram of pertinent electrical components of an illustrative central control unit of the movement assessment system, according to an embodiment of the invention.

Next, with reference to FIG. 4, an exemplary central control unit 24 that may be utilized in conjunction with the embodiments described herein will be described in detail. The central control unit 24 operates as the central hub of the movement assessment system 10. As such, one or more satellite sensor units 22 may operatively communicate with the central control unit 24 using either wired or wireless means. As shown in FIG. 4, the central control unit 24 comprises, inter alia, a processing circuit 52', volatile memory 58' operatively coupled to the processing circuit 52' for storing data during the processing thereof, and a power supply and conditioner 56' operatively coupled to each of the electrical components 52', 58'. As described above for the sensor unit 22, the processing circuit 52' may comprise a microprocessor or other suitable processing means. Also, as described above for the sensor unit 22, the power supply and conditioner 56' regulates the power that is delivered to the electrical components 52', 58' by modifying the level and characteristics thereof (e.g., by regulating the voltage delivered from the power supply 66', 68', 70' by adjusting the voltage level and characteristics in accordance with the specific needs of the electrical components 52', 58'). Referring again to FIG. 4, it can be seen that the power supply or power source for the central control unit 24 may be in the form of a battery 66' disposed within the central control unit 24 itself, a wireless power receiver 68' operatively coupled to a remote wireless power transmitter, and/or a wired power input 70' (e.g., an electrical wire or wires connecting the central control unit 24 to an external power supply, such as a building electrical outlet or receptacle). For example, in some embodiments, the central control unit 24 could be provided with a rechargeable battery 66' and a battery charger configured to connect to the wired power input 70' for charging the rechargeable battery 66' when required. As shown in FIG. 4, no matter which one or combination of the power supplies 66', 68', 70' is used in the central control unit 24, the power supplies 66', 68', 70' are all operatively connected to the power supply and conditioner 56' so that the power delivered thereby can be conditioned prior to being transmitted to the electrical loads (e.g., electrical components 52', 58') in the central control unit 24. If a wireless power receiver 68' is utilized as the power supply for the central control unit 24, the central control unit 24 may be utilized in conjunction with an external wireless power transmitter. Also, in addition to volatile memory 58', the central control unit 24 also may have non-volatile memory 72' in the form of a data storage device, such as one or more compact hard drives, flash drives, memory cards, memory sticks, or any combination thereof.

Also, as shown in FIG. 4, the central control unit 24 may comprise one or more wireless data interfaces 62' for electrically coupling the central control unit 24 to other devices, such as one or more satellite sensor units 22 or a remote computing device. As explained above for the sensor unit 22, the one or more wireless data interfaces 62' may include a Bluetooth device 62a, a Wi-Fi device 62b, and/or a proprietary wireless interface device 62c that utilizes a proprietary communications protocol (refer to FIG. 5). Turning again to FIG. 4, the central control unit 24 may comprise one or more wired data interfaces 64' for electrically coupling the central control unit 24 to other devices, such as one or more satellite sensor units 22, by hard wiring (e.g., an electrical wire or cable), or to a remote computing device. Similar to that described above for the sensor unit 22, the one or more wired data interfaces 64' may include a universal serial bus ("USB") port 64a and/or a proprietary data port 64b (see FIG. 6).

In a further embodiment, the movement and performance assessment system may comprise a remote computing device operatively coupled to the movement and performance assessment apparatus by means of the one or more wireless data interfaces 62' and/or the one or more wired data interfaces 64'. The remote computing device may include a data storage device for storing data acquired by the movement and performance assessment apparatus, and a data processing device (e.g., a microprocessor or other processing means) for analyzing the data acquired by the movement and performance assessment apparatus. The remote computing device may be in the form of a laptop computing device, a tablet, a smartphone, or another type of remote computing device. The remote computing device may be provided with one or more software applications or software programs loaded thereon for tracking the performance of the user during the performance of his or her activities and/or to analyze the results of his or her performance after the activity has been concluded (i.e., the software applications or software programs may enable an "after-the-fact" analysis to be performed on the collected performance data). Advantageously, the post-activity analysis performed by the remote computing device complements the real-time biofeedback provided by the control unit 24 and/or the sensor unit 22. In one or more further embodiments, the remote computing device may be in form of central computing device (i.e., server) for collecting all of the performance data in a central location. The central computing device may comprise a cloud-based computing device for storing the performance data at a remote site.

Also, in one or more further embodiments, the central control unit 24 and/or the sensor unit 22 of the movement and performance assessment system may comprise a counting device configured to measure a number of repetitions of an activity performed by the user. The counting device may be operatively coupled to the data processing device (e.g., the processing circuit 52', which may include a microprocessor) of the central control unit 24 and/or the data processing device (e.g., the processing circuit 52, which may include a microprocessor) of the sensor unit 22 so that the measured number of repetitions are capable of being used in a performance analysis of the user.

In addition, referring again to FIG. 4, the central control unit 24 may include one or more sensors 54' for sensing one or more measurable quantities associated with a subject or user (e.g., an athlete) or an object (e.g., a boat, a golf ball, a handglider, etc.). As explained above for the sensor unit 22, the one or more sensors 54' in the central control unit 24 may comprise an inertial sensor 54a, a magnetometer-type sensor 54b, a load sensor 54c, a motion tracking sensor 54d, an optical sensor 54e, an air pressure sensor 54f, a global positioning system ("GPS") sensor 54g, a body oxygenation sensor 54h, a body temperature sensor 54i, an ambient temperature sensor 54j, and/or a humidity sensor 54k (refer to FIG. 7). With reference again to FIG. 4, the central control unit 24 also may comprise one or more sensory output devices 60' for providing sensory stimuli to a subject or user so as to enable the movement assessment system 10 to provide the subject or user with biofeedback regarding his or her movement. As described above for the sensor unit 22, the one or more sensory output devices 60' may comprise a thermal or heat-based sensor output device 60a, a vibratory sensory output device 60b, a light-emitting sensor output device 60c, an auditory sensory output device 60d, and/or a visual display sensor output device 60e (see FIG. 8).

As illustrated in the block diagram of FIG. 4, the central control unit 24 also may comprise one or more motion tracker reference sources 74' for providing a point or frame of reference for any motion tracking sensors 54d that are used in conjunction with the movement assessment system 10. As explained above for the sensor unit 22, the one or more motion tracker reference sources 74' may comprise a motion tracker reference light source 74a, a motion tracker reference magnetic signal 74b, and/or a motion tracker reference ultrasonic signal 74c (refer to FIG. 9). In FIG. 4, it can be seen that the central control unit 24 additionally may comprise a user interface 76' for allowing the subject or user to interact with the central control unit 24 by controlling the settings thereof, etc. Similar to that described above in conjunction with the sensor unit 22, user interface 76' of the central control unit 24 may comprise one or more buttons 76a or one or more knobs, a display 76b (i.e., visual display), a touch input 76c (see FIG. 10), and/or a keypad or a keyboard. As described above with regard to the sensor unit 22, when the central control unit 24 is provided with a touch-input 76c, the keypad or a keyboard may be in the form of a graphic-based keypad or graphic-based keyboard that is displayed to the user on the touch-input 76c. Also, when the touch-input 76c is provided, the touch-input 76c may comprise one or more graphic-based selection buttons or knobs that enable the user to make various mode selections for the movement assessment system (i.e., to select a particular activity for analysis and/or to select particular aspects of a certain activity for analysis).

Turning once again to FIG. 4, it can be seen that the central control unit 24 may further include a wired peripheral interface 78' for operatively coupling the central control unit 24 to an external peripheral device, such as a pair of audio headphones or a wearable display device (e.g., an optical head-mounted display (OHMD), such as Google® Glass™).

Next, an illustrative manner in which the data processing device (e.g., the processing circuit 52, 52', which may include a microprocessor) of the movement assessment apparatus or system 10 performs the motion-based biofeedback calculations will be explained in detail. In particular, this calculation procedure will describe the manner in which a movement path of the body portion of the user is determined using one or more signals from the at least one sensing device. This calculation procedure will additionally describe the manner in which the movement path determined for the body portion of the user is compared to a baseline movement path, as well as the manner in which it is determined how closely the movement path determined for the body portion of the user conforms to the baseline movement path. Similarly, this calculation procedure will explain the manner in which the velocity profile determined for the body portion of the user is compared to a baseline velocity profile, as well as the manner in which it is determined how closely the velocity profile determined for the body portion of the user conforms to the baseline velocity profile. In one or more embodiments, the velocity profile is the velocity expressed as a function of a scalar parameter representing position along the path of motion. As such, in this case, both the velocity and position must be determined. Also, in one or more embodiments, the term "parameter" shall mean a scalar or a vector parameter. The term "component" shall mean a single scalar component of a vector parameter, or a scalar parameter itself.

In some embodiments, the executed motion is treated in its most general sense, without limiting to any particular set of its parameters, or any particular subsequent transformation of those parameters into a different representation. For example, just measuring the air velocity at the end of a baseball bat is potentially useful by itself to estimate the aerodynamic drag on the bat. The air velocity is relative to the motion of surrounding air, and only available at a point (i.e., thus, in this case, it is not necessary to determine the overall angular velocity of the rigid body of the bat).

It is to be understood that the functionality and calculation processes of the movement assessment apparatus or system 10 described above and hereinafter can be carried out by the data processing device (e.g., 52, 52') utilizing software, hardware, or a combination of both hardware and software. For example, the data processing device (e.g., 52, 52') can be specially programmed to carry out the functionality described hereinafter. In one embodiment of the invention, the computer program instructions necessary to carry out this functionality may be loaded directly onto an internal data storage device (e.g., 58, 58', 72, 72') of the data processing device (e.g., 52, 52') and subsequently executed by the microprocessor of the data processing device (e.g., 52, 52'). Alternatively, these computer program instructions could be stored on a portable computer-readable medium (e.g., a flash drive, a memory stick, etc.), and then subsequently loaded onto the data processing device (e.g., 52, 52') such that the instructions can be executed thereby. In other embodiments, these computer program instructions could be embodied in the hardware of the data processing device (e.g., 52, 52'), rather than in the software thereof. It is also possible for the computer program instructions to be embodied in a combination of both the hardware and the software. Also, in the disclosure, when a reference is made to a data processing device or computing device that is "configured to", "arranged to" and/or "configured and arranged to" perform a specific function (e.g., a data processing device or computing device configured and arranged to perform a specific function), it is to be understood that, in one or more embodiments of the invention, this means that the data processing device or computing device is specially programmed to carry out the particular function (e.g., the data processing device or computing device being specially programmed to perform a specific function).

Figure 26:
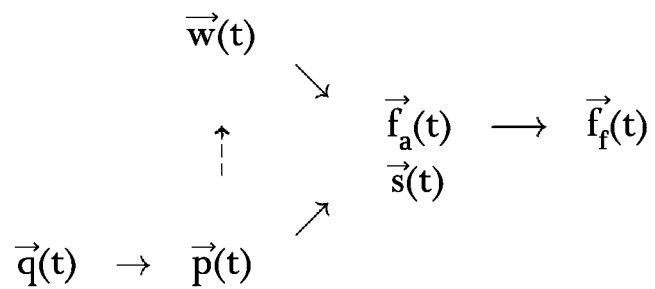
FIG. 26 is a flow diagram of an exemplary motion-based biofeedback calculation process that is carried out by the motion assessment apparatus and system described herein.

The motion-based biofeedback calculation process can be generally described by the flow diagram in FIG. 26. In this figure, $\vec{W}(t)$ represents the reference motion, which can be pre-computed, or derived in real time from the executed motion, or both pre-computed and derived in real time from the executed motion. Also, referring again to this figure, $\vec{p}(t)$ represents the real-time capture of the executed motion, which is obtained from the raw motion data $\vec{q}(t)$. The abstract feedback signal $\vec{f}_a(t)$ in FIG. 26 is generated from both the real-time capture of the motion data $\vec{p}(t)$ and the reference motion $\vec{w}(t)$, while the formed feedback signal $\vec{f}_f(t)$ is obtained from the abstract feedback signal by the process of feedback forming, a provision of the feedback by actuating the formed feedback. In FIG. 26, the selection signal $\vec{s}(t)$ is used for automatic selection of the appropriate reference motion, abstract feedback and formed feedback based on the activity being performed. The notations utilized in FIG. 26 (i.e., $\vec{w}(t)$, $\vec{p}(t)$, $\vec{q}(t)$, etc.) represent that each of these functions comprises a vector-valued function of time t. An arrow indicates that the pointed-to quantity is also a function of the originating quantity, e.g. $\vec{q}(t) \rightarrow \vec{p}(t)$ implies $\vec{p}(t, \vec{q}(t))$: $\vec{p}$ is a function of both time and $\vec{q}(t)$. A dashed arrow indicates that such relationship is optional.

In the illustrative embodiment, the objects being analyzed (e.g., the limbs of the user and various items of sporting equipment are generally modeled as rigid bodies. The movement assessment apparatus or system 10 utilizes rigid bodies as an approximation of more complex physical systems. For example, in the illustrative embodiment of the system 10, the following objects may be approximated as rigid bodies: (i) human body segments (e.g., forearm, thigh, head, etc.), (ii) rigid sports equipment (e.g., baseball bat, tennis racket, golf club), (iii) a handle of a hang glider, a top part of the saddle, etc. The sensor unit 22, through its attachment with a human body segment or the item of sports equipment, becomes integrated with the rigid body (i.e., the motion of the senor unit 22 approximates that of the rigid body).

In the illustrative embodiment, the movement assessment apparatus or system 10 captures several important types of data. First, each of the sensor units 22, and each of the central control units 24 that include the sensor means, capture raw data, which comprises a time series of numeric values that represent the measured parameters of motion. The raw data is both time-discrete and value-discrete. That is, it is defined only at discrete points in time, and can take values from a finite set. The raw data collected by the sensing devices in the sensor units 22, and in the central control units 24, is also uncalibrated (i.e., the raw data does not have any of units of measurements associated with it). Prior to being utilized in the computations performed by the data processing device of the movement assessment apparatus or system 10, the raw data is converted into calibrated data with units of measurement associated therewith (e.g., velocity, position, etc.). In the illustrative embodiment, the calibration process may involve, inter alia, scaling, offset removal, linearization, filtering and sensor fusion. The sensor fusion combines inputs from multiple sensors to overcome their individual shortcomings. For example, output data from redundant sensing devices in a particular sensor unit 22 can be combined to arrive at a single output quantity (e.g., velocity, position, etc.). In the illustrative embodiment of the movement assessment apparatus or system 10, the vector-valued motion parameters may be defined in terms of a reference frame. That is, their values have given numerical values only in the context of such a frame. Also, when there is more than one reference frame available, the motion parameters can be transformed between arbitrary frames. A reference frame, mathematically, is a coordinate system in space (i.e., it has an origin and cardinal directions). In the illustrative embodiment, a natural reference frame, which is denoted N, is rigidly attached to some point on the ground. Such a frame is only approximately inertial, as the earth rotates. It is to be understood that a reference frame itself can be fixed or variable in time. For example, a reference frame attached to a golf club moves and rotates as the club is swung. In addition, as mentioned above, the movement assessment apparatus or system 10 may additionally capture non-motion parameters, which do not pertain to the characterization of the motion itself. For example, ancillary parameters, which are useful in the further analysis of the data, include those that describe the state of the human, the environment, and other things that the human interacts with. For example, a hang-glider pilot's own body temperature, pulse and blood oxygenation can be captured, as well as the environmental temperature, air pressure and air speed.

The raw data utilized in the calculation process may be collected from a multitude of different sensors (e.g., sensor types 54a-54k described above), which may measure any of the following: (i) kinematic parameters of material points or rigid bodies, (ii) kinetic parameters at interfaces between elements of the biomechanical system, (iii) bulk thermodynamic and hydrodynamic parameters, (iv) optical parameters, (v) electrical parameters, and (vi) temporal parameters. The kinematic parameters of material points or rigid bodies may include: (a) position, linear velocity, linear acceleration, and (b) orientation, angular velocity, angular acceleration. The kinetic parameters at interfaces between elements of the biomechanical system may include: (a) contact force, and (b) contact pressure. The bulk thermodynamic and hydrodynamic parameters may include: (a) fluid pressure (e.g., blood pressure, atmospheric pressure), (b) fluid flow rate (e.g. breathing air flow, perspiration flow, blood flow), (c) fluid flow velocity (e.g., relative wind speed), (d) temperature (e.g. body temperature, surrounding air temperature), (e) partial pressure (e.g., partial pressure of $CO_2$ in expired air), and (f) thermal or optical power. The optical parameters may include: (a) radiant flux (e.g., radiant flux due to sunlight), and (b) optical absorption (e.g. in an optical gas analyzer, or in a photopletysmographic blood oxygenation sensor). The electrical parameters may include: (a) electrophysiological potentials (e.g., electrocardiographic or electromyographic), and (b) generally considered impedance (e.g. chest impedance in a breathing sensor). Finally, the temporal parameters may include repetition rate (e.g. heart rate).

In the illustrative embodiment, the sensors 54, 54' (e.g., in sensor unit(s) 22 and central control unit(s) 24) output the raw data $\vec{q}(t)$ in the form of a time series of various components of parameters. That is, the raw data $\vec{q}(t)$ may be expressed as a vector function of time, defined only at discrete points t in time, and comprising n scalar parameters $q_1 \ldots q_n$, each originating in a discrete sensing element:

$$\vec{q}(t) = (q_{r1}(t), q_{r2}(t), \ldots, q_{rn}(t)) \qquad (1)$$

The sensing element may be an integrated multi-channel device, inseparable into constituent sensing elements. Not all components may be defined for a given time point. For example, some signals may be sampled less often than the others. As an example, a sensor unit 22 comprising a tri-axial accelerometer may have captured the following data at 0.5 seconds from the start of capture:

$$\vec{q}_r(0.5 \text{ sec.}) = (312, 495, -1672) \qquad (2)$$

The values in equation 2 above do not have a physical meaning until they are converted or transformed into calibrated data. After calibration, the data $\vec{p}(t)$ is given a meaning of the units of acceleration in a given reference frame.

In one or more embodiments, not all components measured by the sensors may be defined for a given time point. For example, some signals may be sampled less often than the others.

The calibrated, executed motion $\vec{p}(t)$ is obtained from raw data by using an appropriate combination of various processing methods. Generally, each of those methods can be expressed mathematically as a function ($f$) of all current and past raw data, as well as of time itself:

$$\vec{f}_c(t) = f(\{\forall_{t_\alpha < \tau < t} : q(\tau)\}, t) \qquad (3)$$

The time history $\{\forall_{t_\alpha < \tau < t} : q(\tau)\}$ reads a set, for the time $t_\alpha < \tau < t$ since the start of the experiment ($t_\alpha$) up to now ($t$), of the values of the executed raw motion $\vec{q}$. This formulation is general and affords useful flexibility in choosing a calibration process. In some calibration processes, the calibration functions may be time-variant (i.e., their effect on the signals they process may change over time). For example, a scaling and offset removal functions may be temperature-dependent to compensate for the temperature coefficient of the sensor. Faced with varying sensor temperature, the resulting calibration is time-variant. Also, in some calibration processes, the calibration functions may depend on the history of the data. For example, a temperature-dependent scaling and offset removal may also compensate for the thermal constants of the sensor if provided a history of prior values of the sensor's operating environment temperature.

The calibrated executed motion signal can be expressed as a sum of signals from contributing calibrations $\vec{f}_{ci}$, where i is the index of a contributing calibration:

$$\vec{p}(t) = \sum_i \vec{f}_{ci}(t) \qquad (4)$$

A particular contributing calibration can provide just a subset of signals, the others being zero. In one or more embodiments, the following classes of calibration functions are utilized in order to convert the raw data into calibrated data: (i) demodulation, (ii) scaling, (iii) offset removal, (iv) linearization, (v) sensor fusion, (vi) filtering, and (vii) change of reference frame. Demodulation is the process of extracting the measured signal from a representation that was modulated in the transduction process itself. For a particular type of modulation employed in the sensor, the will be a matching demodulation scheme. Many modulation methods are known in telecommunications engineering. They can be utilized to facilitate the transduction process. The transduction itself may also have a property of producing a modulated raw signal that requires demodulation to obtain the direct representation of the measured quantity. For example, in a Doppler velocimeter, the sensor's output is a Doppler signal that must be frequency-demodulated to obtain the velocity signal. Scaling is the multiplication of a raw signal by a scaling constant that relates the physical units of measurement to arbitrary units of raw data. Offset removal is the subtraction of a reference value of a raw signal to relate the signal to a known reference quantity. Often the reference quantity represents a zero physical quantity. In such case, when the sensor output is at the reference value, it is known that the sensor is measuring a zero in terms of physical units of measure of some quantity. Linearization is the adjustment of a raw signal to correct for the non-linear relationship between the raw signal and the calibrated value of the physical quantity intended to be measured by the sensor. The function representing this non-linear relationship may generally be a function of a number of raw or calibrated signals measured by other sensors, and it may be time-variant. Mathematically, such generalization is equivalent to sensor fusion. The choice of naming a given calibration process linearization, not sensor fusion, is arbitrary. It is only meant to indicate that the primary purpose of such fusion is to improve the linearity of a sensor (i.e., it is a hint to the engineer who uses the documentation of such a process). The Extended Kalman Filter is an example of a time-variant linearization function that may be utilized in one or more embodiments of the present invention. Sensor fusion is the combination of raw and/or calibrated data from multiple sensors to produce a calibrated parameter, often overcoming the shortcomings of individual sensors. The same set of raw sensor data can be processed in multiple ways to yield multiple calibrated parameters. The function representing a particular sensor fusion can be as general as necessary. Thus, both time-invariant and time-variant sensor fusion is possible, and both linear and non-linear functions may be employed. An example of a time-variant sensor fusion is a general form of the Kalman filter. Filtering is the adjustment of the frequency-domain properties of the signals. It can involve changing the frequency content and the phase of the signal undergoing filtering. The filtering may be, generally, time-variant (e.g., in a Kalman filter). The calibration function may also involve a change of reference frame. The vector-valued signal may have an associated frame of reference. The subsequent feedback generation may require the signals in a different reference frame. In an illustrative embodiment, the motion parameters or motion data may be transformed between different frames of reference. For example, in an exemplary scenario comprising a polo game, given a linear velocity $^R\vec{v}^M$ and the position $\vec{r}^M$ of a point on the mallet M in the reference frame attached to the rider's saddle R, and given the saddle's angular velocity in relation to ground, $^R\vec{\omega}^M$, we can obtain the linear velocity of the mallet in the natural (ground) reference frame as follows:

$$^N\vec{v}^M = {^R}\vec{v}^M + {^N}\vec{\omega}^R \times \vec{r}^M \qquad (5)$$

The availability of a signal in a given reference frame may be predicated by the chosen sensor arrangement. In the prior example, a motion tracker is tracking the mallet's position in reference to the saddle. An inertial reference mounted on the saddle then tracks the motion of the saddle in relation to an inertial frame. This second reference allows the transformation of the mallet position into an inertial reference frame.

It is to be understood that one mathematical process may have simultaneous functionality of multiple processing methods. The general form of Extended Kalman Filter can perform linearization, sensor fusion and filtering at once. Similarly, a finite-impulse-response (FIR1) or an infinite-impulse-response (IIR2) filter with matrix-valued coefficients, may perform filtering and sensor fusion at once when it acts on a vector-valued signal.

For example, suppose the data is referenced to the natural reference frame:

$$^N\vec{p}(t) = (0.12, -0.91, -0.31)\frac{m}{s^2} \quad (6)$$

This data is discrete in time, thus the value of $^N\vec{p}(t)$ is only defined at discrete values of time t. Rather than being discrete in time, the data may alternatively be a continuous function of time, which is defined on a certain continuous time segment $t_\alpha \leq t \leq t_\omega$. The continuous form is more succinct to write and alleviates the application-specific choices of numerical approximations. Also, the data may be mathematically transformed from a continuous form to discrete approximations (i.e., the data may be discretized). For example, integration may be approximated by summation according to a chosen numerical integration scheme.

Next, the reference or baseline motion utilized in conjunction with the embodiments of the present invention will be described. The components of the reference motion form a superset of the parameters of the executed motion:

$$\vec{w}(t) = (w_1(t), w_2(t), \ldots, w_n(t)) \quad (7)$$

where for a certain possibly empty subset of indices j, the reference component j is the $i_j$-th component of the executed motion $w_j(t) = p_{i_j}(t)$.

For example, the reference signal can include a representation of the surface to which a motion should be constrained. Such a parameter is not present in the executed motion signal. Such a reference can be constant (e.g., a fixed terminal velocity of the piano key strived for when learning a particular expression level when playing a keyboard). The reference signal can be classified according to various aspects of its derivation.

First of all, the reference signal may be classified according to its temporal aspect. In particular, the reference signal can be based on an executed motion in the past or present, or on the limits of the motion feasible in the future. In some embodiments, the reference signal can be based on a captured prior performance. It may be the performance of the same subject, used to elicit improvement of performance, or to recover performance lost between seasons, or due to injury. Alternatively, the prior performance may belong to a high-level performer, to direct the subject's training towards such a standard.

In some embodiments, the executed motion underway could be the sole source of the feedback. The reference signal may be derived from any temporal subset of the motion. As one example, the distance from the starting point of the motion could be used to signal a sufficiently long draw of a bow. The reference is based on a very short past time segment of the motion. As another example, suppose an ideal swinging motion is to follow a particular surface, e.g. a plane or a cylinder of a given radius of curvature. A least-square-distance fit of the surface to the path of the motion executed thus far can be used to compute the normal distance of the currently executed position from the surface. The time-variant reference surface can be fixed—made invariant—after some criterion is met, e.g., after the motion has covered a set distance, or a set swing angle, or after reaching a set swing velocity. The reference signal may be derived from the segment of the motion between its start and the time a chosen criterion is met. The criterion may be null: then the entire motion up to now forms the reference.

In some embodiments, the reference signal can also be based on predicted future motion. The predicted future motion can take into account the performance limitations of the human musculoskeletal system. For example, suppose a given motion is to approach a target within a particular velocity range. In a particular configuration of the body segments, there are biological limits to the available torques and torque-change-rates. At a given time instant during the motion, it is possible to estimate how close to the biological limits the future motion must come to arrive at the target. It is thus possible to signal a-priori how close is the current motion is to precluding achievement of a correct result in the future.

Secondly, the reference signal may be classified according to its synthetic aspect. The degree of a reference signal's dependence on any captured motion can vary, from no dependence to a full dependence. The less dependent the reference signal is on a captured motion, the more synthetic it becomes. The degree of syntheticity may be defined using the information-theoretic concept of conditional entropy. Informally, the more entropy of the captured motion is preserved in the reference signal, the less synthetic it is. Formally, the larger the entropy of the captured motion $\vec{p}$ conditioned on the reference motion $\vec{w}$, the more synthetic the reference motion is. The entropy of a signal, informally, is the amount of information carried by the signal. It is preconditioned on what is known a-priori. For example, considering the toss of a coin, the entropy of the resulting data is 1 bit, since the outcome is binary (one of two values). If the coin toss is performed with an unfair coin that is known to always give tails, the entropy is zero, since the outcome of the coin toss does not give any new information (i.e., one can always anticipate the result).

The non-synthetic reference is largely dependent on the captured motion. It preserves a relatively large amount of data from the motion. A representative example would be a captured motion that passes through a low-pass filter: it removes some frequency content from the reference, while passing the frequency components below the cut-off point unaltered. The dimensionality and units of measurement of the captured data are preserved, but some of the possible variability in the captured motion is lost.

The synthetic reference is a parametrized representation of the captured motion. The number of the parameters is much smaller than the number of values needed to represent the captured motion. The choice of the function(s) implementing such a reference is tailored to capture the aspects of the motion that are useful in subsequent generation of the feedback. For example, in training a particular curveball pitch, the reference may be the development in time of the ratio of energy between the rotational and linear motion of the ball—a scalar parameter. The full information about the motion of the ball, in comparison, has 6 degrees of freedom. The synthetic reference, in spite of being a parametrized representation of a motion, may still result in the same dimensionality and units of measurement of the resulting signal. In spite of it, the outputs of the synthetic reference are not able to accurately represent every possible captured motion.

Also, the selection of parameters constituting the reference motion signal can have a major impact on the usability and effectiveness of the feedback provided to the user. As such, one has to decide when to use parameter(s) from the captured motion versus a more synthetic parameter derived from those parameters. The functions presented below may also be applied in other areas of the processing chain, such as (i) during feedback forming, if the interaction of the nonlinearities of the synthetic parameter function with those of the abstract feedback function makes such choice preferable over the inclusion of the parameter in the reference; and (ii) during agreement (as described hereinafter), when the same synthetic parameter is to be compared between the reference and the executed motion.

The derivation of such synthetic parameters can be performed using various techniques. The techniques also can be combined. For example, given a three-dimensional (3D) vector parameter, one can compute the time derivative (velocity) of the vector, obtain the rotational component of the velocity, represent it with an Euler axis and an angle, project the Euler axis onto a two-dimensional (2D) plane, obtain the projection's magnitude and angle, and finally derive the angular velocity from the angle. In one or more embodiments, the synthetic parameters may be derived using one or more of the following techniques: (i) projection, (ii) component selection, (iii) change of representation, (iv) time derivative and integrals, (v) energy and power, (vi) statistical measures, (vii) curve and surface fitting, (viii) domain transformations, (ix) event detection, (x) normalization, and (xi) truncation. Initially, with projection, a vector-valued parameter of a certain dimensionality m is projected onto a generalized lesser-dimensional surface, yielding a vector-valued parameter of a smaller dimensionality $1 \leq n < m$. When component selection is used, a subset of a vector's components may be selected for further use, for example, only the (x, y) components of an (x, y, z) vector.

Change of representation may also used as the technique for deriving the synthetic parameters. The vector values may have multiple equivalent representations. Either a part or all of the alternate representation constitutes the newly synthesized parameter. An alternate representation may exhibit mathematical properties that make it more useful for feedback generation—for example, it may convert a vector to its orientation. The representations may include: (i) magnitude with orientation angles, (ii) quaternions (without limitation to unit quaternions), and (iii) radial and rotational (tangential) components of a velocity vector when given the associated position vector. Parameters whose components have the meaning of angles can be equivalently represented as: (i) rotation matrices, (ii) Euler axis and angle, (iii) Euler angles, wherein multiple choices of rotation axes exist (e.g., an alternate set of rotation axes is commonly called Tait-Bryan angles), (iv) quaternions, (v) Cayley-Klein parameters, and (vi) Rodrigues parameters.

Time derivatives and integrals are another technique for deriving the synthetic parameters. A vector's time derivatives and time integrals may be used to convert between position, velocity, acceleration and jerk in terms of both linear and rotational motion. When energy and power is the technique employed for deriving the synthetic parameters, kinetic and kinematic parameters may be combined to derive the energy of a part of the system (the body), or change in energy—the power generated or absorbed by the system. The synthetic parameter derivation technique may also utilize statistical measures. In particular, mean, variance, covariance, and other statistical measures of one or multiple signals may be computed. The measures may be computed over all data since the start of the experiment, or a temporal subset. The temporal subset referenced to the present is also known as a rolling window.

The technique for deriving the synthetic parameters may also comprise curve and surface fitting. The prescribed motion, whether derived from a prior executed motion or arbitrarily specified, can be represented and substituted with a function that best fits such data according to some error minimization criterion. The mathematical representation of a fitting curve or surface can be chosen from the explicit, implicit and parametric representations. Examples of some fitting functions that may utilized include: (i) scalar-valued and vector-valued polynomials, (ii) Bezier curves and surfaces, (iii) B-Spline curves and surfaces, (iv) non-uniform rational B-spline (NURBS) curves and surfaces, and (v) T-Spline surfaces.

Domain transformations are another technique for deriving the synthetic parameters. The signal can be transformed from the time domain to another domain, such as frequency or quefrency domain. The time-to-frequency transform is called the Fourier transform and yields a spectrum. The time-to-quefrency transform yields a cepstrum. The synthetic parameter derivation technique may also comprise event detection. With this technique, events, found by placing constraints on parameters, can be marked and their properties constitute a new set of parameters. For example, the temporal or spatial location of maximum (peak) or minimum values can be extracted from the signal. The reversals of motion direction can also be detected. Normalization may also be used as the synthetic parameter derivation technique. A reference motion may be both spatially and temporally normalized. Spatial normalization limits the spatial extent of the motion to arbitrary boundaries, for example within a cube having a unit (1) side length. Temporal normalization limits the duration of the reference motion, for example to one (1) unit of time. The normalization techniques include peak detection, scaling and truncation. The latter two can be either or both spatial and temporal. Finally, the synthetic parameter derivation technique may comprise truncation. That is, parts of the reference motion that are deemed not useful by other criteria can be truncated by either removal of data for given time instants, or constrainment of values within chosen bounds. For example, in golf, one may deem unnecessary the data prior to the commencement of ball-directed motion of the putter.

Figure 27:
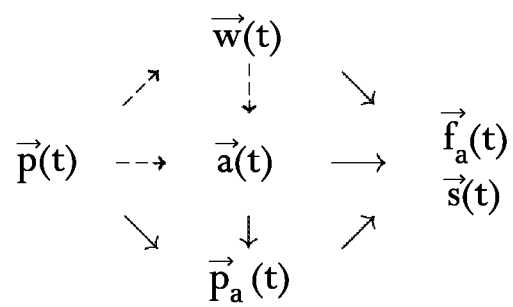
FIG. 27 is a flow diagram illustrating an exemplary abstract feedback signal generation process that is carried out by the motion assessment apparatus and system described herein.
Figure 28:
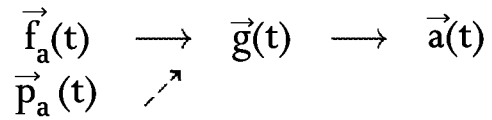
FIG. 28 is a flow diagram illustrating an exemplary adaptation signal generation process that is carried out by the motion assessment apparatus and system described herein.

Now, the abstract feedback signal (i.e., the sensory output signal) will be described. While the formed feedback signal is concerned with the manner in which the feedback is delivered to the human user, the abstract feedback signal is concerned with the manner in which the feedback signal is generated or obtained from the motion data. In general terms, the abstract feedback signal $\vec{f}_a(t)$ is a measure of a deviation between the executed motion $\vec{p}(t)$ and the desired, or reference, motion $\vec{w}(t)$. The feedback signal is abstract from the form of the feedback itself to the user. The abstract feedback signal is not tied to any particular means of presentation to the user, such as a visual device, audio device, or tactile device that delivers perceptible feedback to the user. The abstract feedback generation process can be generally described by the flow diagram in FIG. 27. In general, the abstract feedback generation involves the following sub-operations: (i) agreement, (ii) comparison, and (iii) adaptation. First, with agreement, the executed motion $\vec{p}(t)$ is brought to the feedback-agreeing form $\vec{p}_a$. The feedback-agreeing form may be parametrized by an adaptation input $\vec{a}$. This form agrees with the dimensions, reference frames and units of the reference motion $\vec{w}$. Secondly, with comparison, the reference motion $\vec{w}$ and the feedback-agreeing form $\vec{p}_a$ is used to compute the abstract feedback $\vec{f}_a$. The latter can be parametrized by an adaptation input $\vec{a}$. Thirdly, with adaptation, the executed motion and the reference motion can provide input to an adaptation function $\vec{a}(t)$. The adaptation values are used to adjust the sensitivity, temporal and spatial, alignment and other parameters of the agreement and comparison processes in order to provide useful feedback.

Next, the selection signal $\vec{s}(t)$ will be described. The selection signal $\vec{s}(t)$ is used for selection of the reference motion, the abstract feedback and the formed feedback schemes according to the activity being performed. Because the selection signal generation is performed fundamentally similarly to the abstract feedback generation, it will be described in conjunction with the discussion of the abstract feedback signal. The selection signal $\vec{s}(t)$ allows the system to adjust the one or more parameters of the baseline movement path and/or the velocity profile to accommodate a plurality of different activities performed by the user. Also, in one or more embodiments, the selection signal $\vec{s}(t)$ may be used to select the particular portion of the abstract feedback signal $\vec{f}_a$ that is used to provide feedback to the user during the performance of a particular activity. For example, if the user is hitting a tennis ball with a tennis racket, the abstract feedback signal $\vec{f}_a$ may comprise a first set of parameters that are associated with whether or not the tennis ball is being struck with the center of the racket, and a second set of parameters that are associated with whether or not a sufficient sliding motion is being imparted on the tennis ball by the tennis racket so as to induce ball spin. In this example, if the user is concerned with the ball center position but not ball spin, the selection signal $\vec{s}(t)$ selects the first set of parameters of the abstract feedback signal $\vec{f}_a$, which are directed to the ball center position. Conversely, if the user is concerned with ball spin but not the ball center position, the selection signal $\vec{s}(t)$ selects the second set of parameters of the abstract feedback signal $\vec{f}_a$, which are directed to the sliding motion that induces ball spin. In this example, the selection signal $\vec{s}(t)$ is utilized to select one portion of the abstract feedback signal $\vec{f}_a$ or the other in order to control the type of feedback that is outputted to the user. Thus, advantageously, the user is able to focus on the portion of the executed motion that is most pertinent to his or her own performance enhancement plan.

The plurality of different activities performed in succession by the user necessitates the selection of a relevant reference motion, abstract feedback and formed feedback schemes. Such selection from a list of activities, performed manually by the trainee, may disrupt the flow of the training. As such, it is beneficial to automate the selection by determining the type of activity being performed without explicit user input to that effect.

The activity matching is accomplished by comparing the executed motion $\vec{p}(t)$ with each reference motion $\vec{w}$ from a set of reference motions, representing the anticipated activities, and selecting the closest match. The reference motion $\vec{w}$ may have a plurality of different reference motions contained therein. For example, there may be three (3) different reference motions included within the reference motion signal $\vec{w}$. The automatic selection process for the reference motion $\vec{w}$ may determine the closest match of the three (3) reference motions in the reference motion signal $\vec{w}$, and use the reference motion determined to be the closest match as the reference motion for the activity being performed. As such, it is a case of signal classification. In the simplest case, the signal used for such a comparison may be the same as the abstract feedback signal. That is, in the example above, the abstract feedback signal $\vec{f}_a$ may be used to determine the closest match of the three (3) reference motions in the reference motion signal $\vec{w}$.

In one or more embodiments, each activity in the set of the anticipated activities may optionally be assigned a weight that favors certain selected activities over the others. Such weights may be adjusted to favor the most recently performed activities. This limits the chance of erroneously switching an activity due to an occasionally poor performance that happens to be more similar to some other anticipated activity. For example, as an individual performs a particular activity over time, weights are continually assigned to reference motions corresponding to each activity in a set of anticipated activities. Over the course of performing the particular activity, one or more reference motions corresponding to one or more respective activities in the set of anticipated activities becomes significantly more heavily weighted than the other reference motions corresponding to the other respective activities in the set of anticipated activities. As such, for example, when the individual becomes gradually more tired during the performance of the activity, the weights applied to the reference motions of the activities in the set of anticipated activities prevent the movement assessment apparatus from erroneously switching to an incorrect reference motion as a result of the individual's decreased performance.

Also, in one or more embodiments, the system incorporates one or more devices that enables the activity selection by an explicit input from the user. For example: providing a "select enable" switch on the club. The selection signal would only be used to switch an activity if the motion was performed with the button being depressed. Another enable mechanism can leverage the choice of the implement used to execute the motion. For example, the use of a golf putter would limit the anticipated activity set to those relevant to putting, whereas the use of a driver club would similarly limit the anticipated activity set to those relevant to drives.

To facilitate the accuracy of the selection process, the selection signal for each anticipated activity can be continuously generated even if the explicit user input bars the selection. Such signal can be used by a machine learning algorithm to further continuously adjust the thresholds used to classify the motion as belonging to a certain anticipated activity.

Now, the agreement sub-operation will be explained in detail. The feedback-agreeing form has the same number of dimensions, and its components have the same units of measurements, as the reference motion. The meaning, or semantics, of the parameters in both forms also typically match, unless a cross-referenced feedback is desired. For example, one can train the motion of one arm to match the motion of another arm. The reference motion's signal applies to the left arm, while the executed motion signal applies to the right arm. The semantic mismatch between them is desirable under the circumstances.

The data provided by the adaptation input can be used to adjust the parameters of the agreement computations. For example, the bandwidth of a filter applied to the motion data may be increased as the trainee's performance improves.

The agreement functions used depend both on the choice of the parameters forming the executed motion, and the parameters forming the reference. The use of synthetic reference parameters may necessitate the computation of the same synthetic parameters from the motion signal during the agreement. Many of the functions useful for the calibration of the executed motion signal can be utilized here as well. For example, scaling may be used to bring the units of measurement into agreement (e.g., the velocity in the reference motion might be represented using the International System of Units (SI units), while the velocity in the captured motion may be expressed in terms of the Mach number obtained from an air probe). As another example, offset removal may be used to bring the zero reference point (intercept) of the executed motion into agreement with the one used for the reference. For example, a reference acceleration signal might not include the 1 g offset due to the acceleration of gravity at the site of the executed motion. As yet another example, sensor and component fusion may be used to reduce the dimensionality of vector-valued parameters, or to convert vector-valued parameters to scalar ones. For example, suppose the feedback shall be an indication of how closely a curveball's rotational velocity is to a desired target value. The reference motion consists only of a scalar magnitude of the angular velocity vector. The captured executed motion may consist of the three-dimensional (3D) positions of a set of three reference points on the surface of the ball. The reference point positions, having nine (9) components in all, need to be reduced to a single-component angular velocity. As yet another example, filtering may be used to remove the frequency components of the captured motion that are not deemed useful for the generation of the feedback. For example, a bandpass filter might be used to select the base harmonic of the position of a baton twirler's baton.

Next, the manner in which the movement path and/or the velocity profile of the user is compared to a respective baseline movement path and/or velocity profile will be described. In addition, the manner in which it is determined how closely the movement path and/or the velocity profile of the user conforms to the respective baseline movement path and/or velocity profile will be explained.

While in some embodiments, the feedback's measure of deviation may be a simple mathematical subtraction, in other embodiments, the feedback's measure of deviation may be any function that depends on time itself and the time history of executed motion and reference motion and optional adaptation, such as that represented by the following equation:

$$\vec{f}_a(t) = f(\{\forall_{t_a < \tau < t} : (\vec{p}(\tau), \vec{w}(\tau), \vec{a}(\tau))\}, t) \quad (8)$$

The time history $\{\forall_{t_a < \tau < t} : (\vec{p}(\tau), \vec{w}(\tau), \vec{a}(\tau))\}$ reads a set, for the time $\tau : t_a < \tau < t$ since the start of the experiment ($t_a$) up to now (t), of the pairs of the executed and reference motions and adaptation, $\vec{p}$, $\vec{w}$, and $\vec{a}$, respectively. The abstract feedback may contain multiple measures of the deviation, derived from one or more reference motions.

Exemplary techniques to compare the executed motion to the reference are explained below. Such computations may be combined, for example, two signals may be subtracted and then a variance of the result computed. Some functions listed below take single parameters. Those functions are used following another operation that has combined the executed and reference parameters.

Subtraction of the executed and reference parameters may be done using one of the following functions:

$$\vec{w} - \vec{p} \text{ or } \vec{w} + \vec{p}, \text{ depending on mutual orientation of vectors,} \quad (9)$$

$$\|\vec{w} - \vec{p}\|, \text{ where } \|\circ\| \text{ is the Euclidean vector norm,} \quad (10)$$

$$\sqrt{w^2 - p^2}, \text{ where } w \text{ and } p \text{ are scalar,} \quad (11)$$

Cosine Similarity is defined as:

$$\frac{\vec{w} \cdot \vec{p}}{\|\vec{w}\| \, \|\vec{p}\|}, \text{ where "·" is the dot product, and } \|\circ\| \text{ is the Euclidean norm,} \quad (12)$$

Tanimoto metric is defined as:

$$\frac{\vec{w} \cdot \vec{p}}{\|\vec{w}\|^2 + \|\vec{p}\|^2 - \vec{w} \cdot \vec{p}} \quad (13)$$

where "·" is the dot product, and $\|\circ\|$ is the Euclidean norm.

Statistical measures of covariance and correlation act on two or more parameters selected from the executed and/or reference motions. The mean and variance act on a single parameter. Convolutional measures are computed by first convolving the executed motion with the reference motion, then applying another self-comparison technique, such as peak detection, to the result. The output of the comparison function constitutes a measure of deviation between the reference and executed motion. Such abstract feedback is then formed and presented to the subject. The scaling of the abstract feedback in relation to the formed feedback may be fixed or adaptive, depending on the task and chosen training strategy.

Hereinafter, the manner in which one or more parameters of the baseline movement path and/or the velocity profile may be adjusted to accommodate at least one of: (i) a skill level of the user with respect to a particular activity, (ii) a particular movement style of the user, and (iii) physical limits of the user, will be described. In addition, the manner in which the sensitivity of the biofeedback is adjusted so as to accommodate users of different skill levels will be explained.

The adaptation signal $\vec{a}$ may be used to adjust the parameters of the agreement and abstract feedback generation operations. It is of use to tune those operations to the skill level of the user with respect to a particular activity, a particular movement style of the user, and his or her physical limits. In one or more embodiments, the adaptation signal $\vec{a}$ is used to adjust how the reference signal $\vec{w}$ is calculated. The adaptation signal $\vec{a}$ may be based upon user input. For example, the user may select some aspect of the reference signal that he or she is not interested in receiving feedback on. For example, for a particular user, feedback may not be provided for an overstressed part of the body (e.g., for a user performing a dancing exercise, weights are lowered for landing when the dancer has an injury related to the landing motion). As such, the adaptation signal $\vec{a}$ is used to adjust the feedback by taking into account the physical limits of the user. The adaptation signal $\vec{a}$ may also account for different ways of performing the same task. The adaptation signal $\vec{a}$ may also modify the reference motions themselves. For example, for an activity that is performed by both children and adults, the adaptation signal $\vec{a}$ may institute a "child mode" that adjusts for the physical differences in the movement of a child versus an adult. Advantageously, the adaptation signal may be used to minimize the parameters that are required to be input by the user. As illustrated in the signal process flow diagram of FIG.

28, one way of performing parameter adaptation is optimization towards a given goal, given a goal function $\vec{g}(t)$. The goal function takes the abstract feedback signal $\vec{f}_a(t)$ and optionally the adapted executed motion $\vec{p}_a(t)$, and provides input that steers the adaptation signal towards the goal. This optimization problem, albeit generally nonlinear, may be solved using various known optimization techniques. The goal function must be chosen such that it leads to the feedback that is useful in the training process. It should address the following variability inherent in the execution of the motion: (i) skill level, (ii) movement style, and (iii) physical limits of the user.

Initially, with respect to skill level, the abstract feedback can be used as an estimate of the difficulty of the activity. The goal is to achieve the feedback such that the activity appears, by the feedback provided to the user, to be neither extremely challenging nor extremely easy. This can be achieved by adapting either the gain or the reference feedback level. If the reference level is being adapted, then the gain can be selected to maintain the expected level of variance of the feedback signal, considered within one or more repetitions of the motion.

Secondly, with respect to the movement style, the abstract feedback signal can be dependent on multiple aspects of the motion as well as on multiple aspects of the reference motion, as defined by the different computations that are performed in parallel on the same executed and reference motions to obtain the feedback. Each of those dependencies can be weighted. The weights are subject to adaptation. The weights can be optimized to minimize the influence of those aspects of the motion that are highly variable and show no ongoing improvement. As other aspects of the motion improve, the weights of such suppressed aspects of the motion can be periodically re-enhanced to probe whether further improvement can be achieved. The schedule of such re-enhancements can be itself optimized to minimize nuisance negative feedback, based on established models of human learning, such as those in the SuperMemo body of work (see e.g., http://www.supermemo.com/english/algsm11.htm). If multiple styles of motion performance are a-priori recognized for a given activity, the reference motion can include them in parallel. The goal is to reinforce the one of the multiple styles of reference motion that best approaches the executed motion.

Thirdly, with respect to the physical limits of the user, the abstract feedback for each executed motion has a certain distribution of values across multiple trials. The physical limitations can be extracted as the parameters of those distributions. For example, a performance well under the physical limits may exhibit a symmetric distribution, while a performance at the physical limit may exhibit an asymmetric distribution. The extracted parameters can be used with biomechanically derived models of human performance to quantify one or more aspects of the user's physical limitations. For example, a certain motion may be kinetically limited to a maximum torque due to the cross-section of a key muscle generating the motion. Apart from the muscle's cross section, the biomechanical model may include an estimate of the anaerobically available energy stored in the volume of the muscle. Such energy store is depleted with repeated motions. The estimate can be used to adapt the virtual torque that would have been necessary to produce the reference motion in a similarly built individual.

In the illustrative embodiment, the acquired or captured data may be used to compare the motion to some prescribed form, and to provide real-time feedback to the human user as to possible deviations from the prescribed form. The feedback to the user may be provided by a plurality of different means. These means actuate, or act upon, a formed feedback signal $\vec{f}_f(t)$. The formed feedback may be specific to a given means of presentation. Some of the functions used for calculation of the synthetic reference motion may also form the feedback (e.g., refer to the choice of synthetic parameters explained above). For example, as described above, the feedback may comprise aural or auditory feedback from an auditory sensory output device 60*d* (see FIG. 8). In one or more embodiments, the auditory sensory output device(s) 60*d* may be in the form of headphones, or in the form of sound sources installed on equipment or in the environment the human interacts with (e.g., one or more speakers may integrated into the sensor unit 22 or the central control unit 24). Also, the sound emitted by the auditory sensory output device 60*d* may represent one or more feedback signals in one or more of the following exemplary ways: (i) by the timbre/texture of the sound, (ii) by the volume and spatial localization of the sound, (iii) by the pitch and harmonic content, and/or (iv) by the envelope (the attack, sustain, hold and decay aspects of the sound). The formed feedback signal represents the sound pressure over time.

As another example, as also described above, the feedback may comprise visual feedback from a light-based sensory output device 60*c* or a visual sensory output device 60*e*. The visual feedback adds or changes the light perceived by the human eye in various ways, such as by modulating the brightness or focus of the perceived scene, using optoelectronic shutters, variable lenses, or augmented reality systems. Such feedback can modify the visual perception by providing visual cues not ordinarily present. For example, it can present a stimulus that is temporally or spatially synchronized to the desired event. More specifically, for example, spatially or temporally non-essential aspects of the viewed scene can be defocused, have their contrast reduced, or be blanked out, while the essential aspects of the scene can have their focus, contrast, or color saturation improved. The visual feedback may also add or change the light perceived by the human eye by adding imaged or non-imaged sources of lights that can, for example, prompt for attention, add information related to the external event and/or the performance of the human. The formed feedback signal represents the parameters of the image modulation, the image contents of the augmented reality display, the intensity and color of non-imaged sources of light, etc.

As yet another example, as mentioned above, the feedback may comprise haptic or tactile feedback from a heat-based sensory output device 60*a* or a vibratory or vibration-based sensory output device 60*b*. This type of feedback exerts tactile and kinetic stimuli (i.e., kinetic stimuli having to do with/of forces). For example, reaction wheel(s) on a golf club or a tennis racket can provide a resisting torque to guide the trajectory of the swing to give a perception of directed resistance not normally experienced. As another example, a force feedback on a piano key can provide timed resistance to guide a player who is learning to play the piano into the proper tempo or rhythm. The haptic sources can actuate based on one or more feedback signals in one or more of the following exemplary ways: (i) by tactile sensations, such as texture, sensation of hot or cold, change in friction (for example by using a controlled vacuum source to control adhesion of skin to the surface), vibration, pressure, etc.; (ii) by force feedback, by imposing additional force and torque loads on the human through the objects the human interacts with. For example, force feedback may be provided by inertial reaction forces and torques, thus it can be exerted on objects that can otherwise freely move through the space, such as bats, clubs, racquets, balls, etc., without having the forces flowing through a structure attached to the ground or the user/performer. The formed feedback signal represents the kinetic and thermodynamic parameters to be actuated.

An exemplary software code that is capable of carrying out some of the fundamental functionality described herein is provided at the end of this written disclosure. The exemplary code generates a simulated executed motion for softball batting, and provides audible feedback for the vertical location of the bat-on-ball. Graphical output generated by the exemplary software code is illustrated in FIGS. 29-35.

Figure 29:
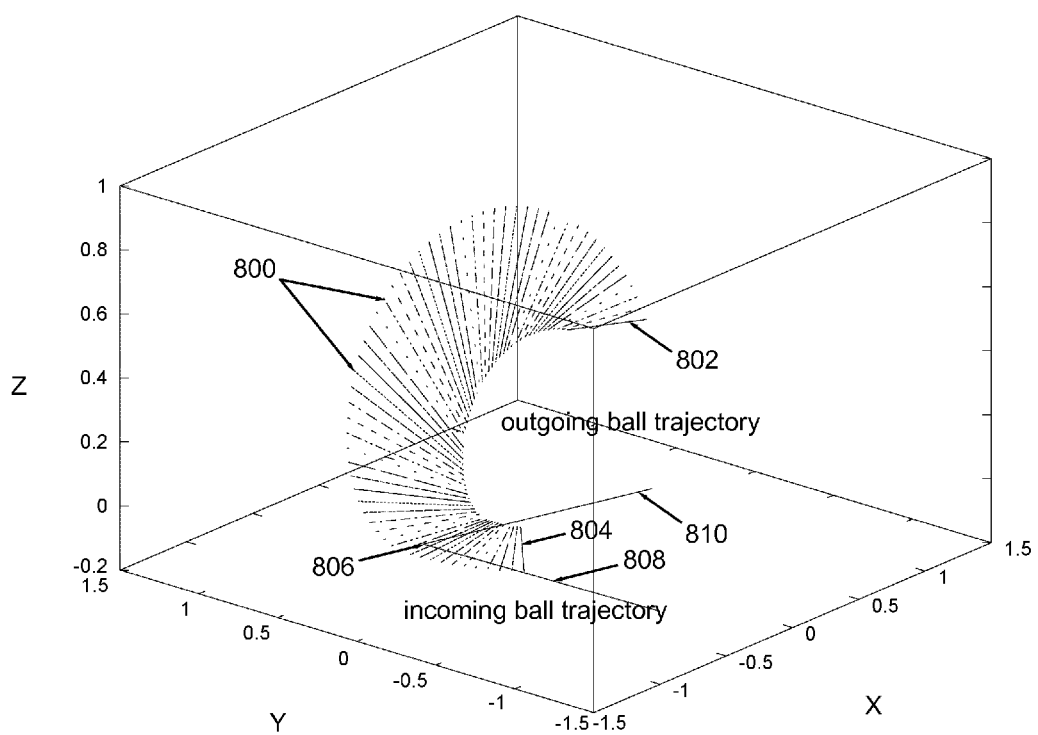
FIG. 29 is a three-dimensional (3D) plot illustrating a bat swing and ball trajectory generated by the exemplary movement assessment software code described herein.
Figure 30:
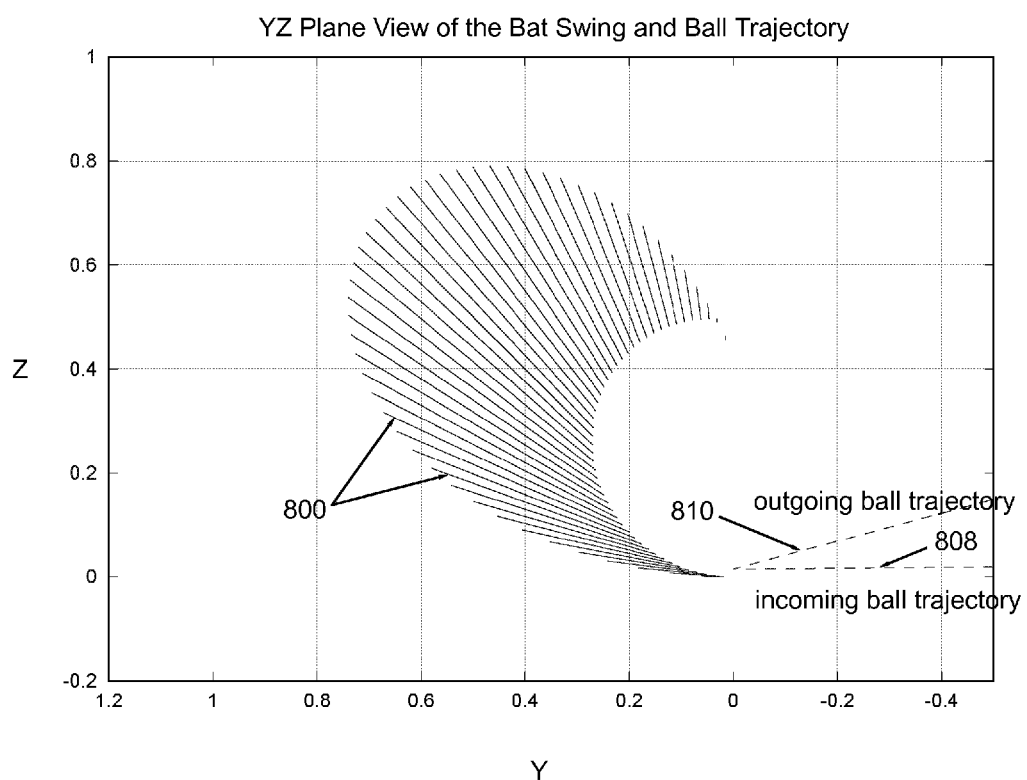
FIG. 30 is a plot illustrating a bat swing and ball trajectory in the Y-Z plane as generated by the exemplary movement assessment software code described herein.
Figure 31:
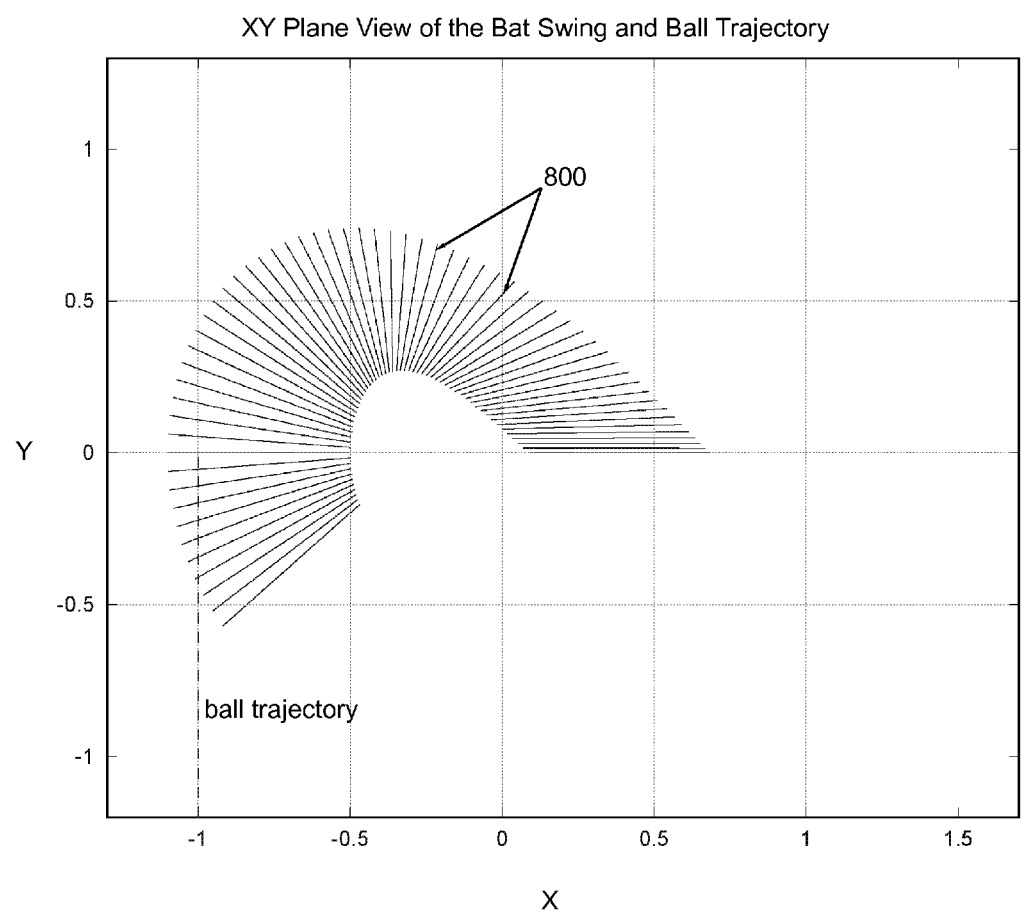
FIG. 31 is a plot illustrating a bat swing and ball trajectory in the X-Y plane as generated by the exemplary movement assessment software code described herein.

In FIGS. 29-31, the bat swing trajectory and the ball trajectory are depicted in graphical form. FIG. 29 illustrates a three-dimensional oblique view of the bat swing and ball trajectory, while FIGS. 30 and 31 illustrate the bat swing and ball trajectory in the Y-Z and X-Y planes, respectively. Initially, referring to the oblique view of FIG. 29, it can be seen that the displacement of the bat throughout the course of the swing is diagrammatically represented by a series of lines 800 (i.e., the motion of the bat is modeled based upon two points disposed on the centerline of the bat). At the beginning of the swing, bat is disposed in an upper, generally vertical position 802, while at the end of the swing, the bat is disposed in the generally horizontal position 804. Prior to the end of the swing, in the exemplary motion modeled by the software code, the bat contacts the ball at a point of contact 806. As shown in FIGS. 29 and 30, prior to contacting the bat, the incoming ball trajectory 808 is generally horizontal. After contacting the bat, the outgoing ball trajectory 810 has a generally diagonal upward path of flight.

Figure 32:
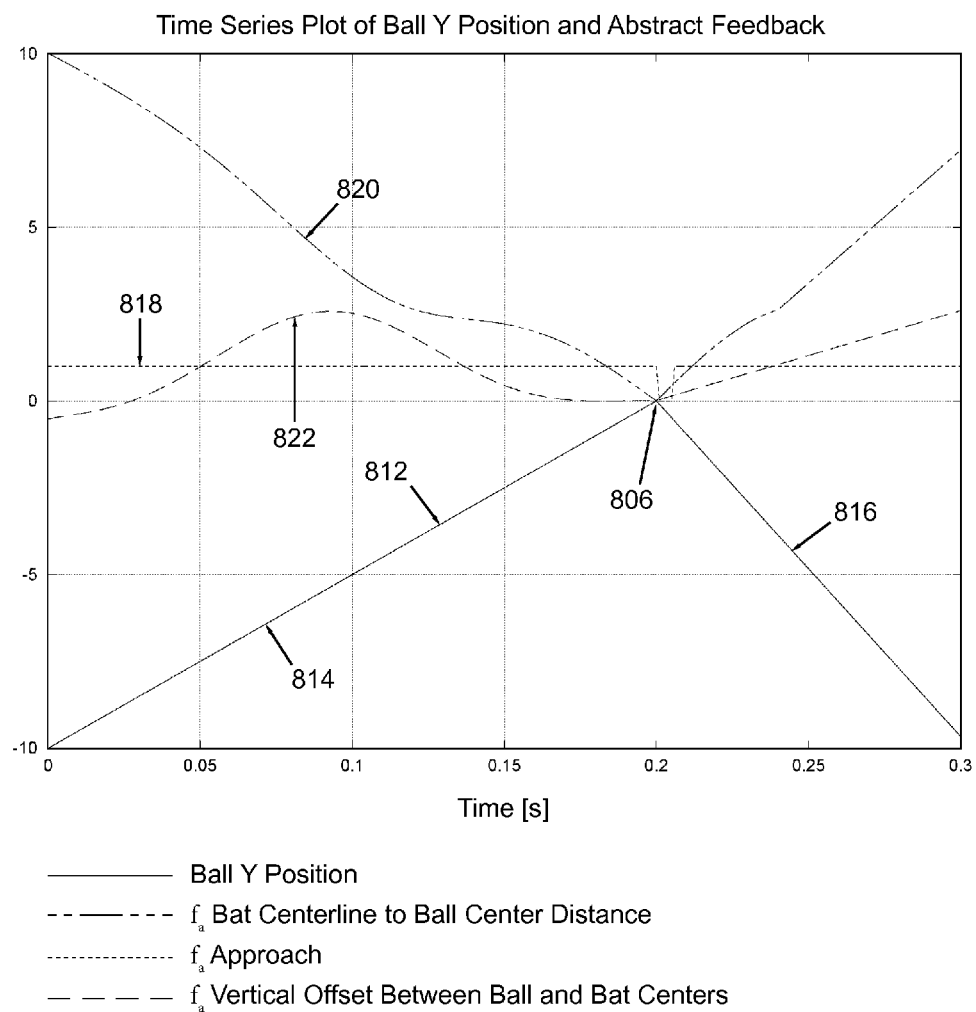
FIG. 32 is a time series plot illustrating ball Y position and abstract feedback as generated by the exemplary movement assessment software code described herein.

Turning to FIG. 32, a time series plot of the ball y-position and abstract feedback is illustrated. In general, the exemplary software code provided herein determines how closely the ball point of contact coincides with the centerline of the bat. If the ball contacts the bat significantly underneath the bat centerline, then the ball will most likely be directed towards the ground (i.e., a ground ball). Conversely, if the ball contacts the bat significantly above the bat centerline, then the ball will most likely be directed almost straight up in the air (i.e., a pop-up or pop fly). As shown in FIG. 32, the y-position of the ball 812 comprises an approaching portion 814 until the point of contact 806 with the bat, and then a leaving portion 816 following the point of contact with the bat. The time series plot of FIG. 32 further illustrates the abstract feedback approach 818, an abstract feedback bat centerline to ball center distance curve 820, and an abstract feedback vertical offset between ball and bat center curve 822. In order to acquire the bat and ball data required to generate the output illustrated in FIGS. 29-35, a plurality of markers could be provided on the bat and the ball such that the motion of the bat and the ball could be acquired by a marker-based motion tracking system. Alternatively, the bat and the ball could be provided with suitable inertial measurement units and tracking devices disposed thereon, such as those that will be described in conjunction with the scenario of FIG. 19 hereinafter.

In the output of the exemplary software code, the first component of the abstract feedback (f_a) is the bat centerline to ball center distance. The second component of the abstract feedback is the approach flag: true (high value) when the ball is approaching the bat; switches to false (low value) when the ball starts to recede. The third component of the abstract feedback is the vertical offset between center of the ball and the bat centerline. The vertical offset between center of the ball and the bat centerline is used to generate the formed feedback.

Figure 33:
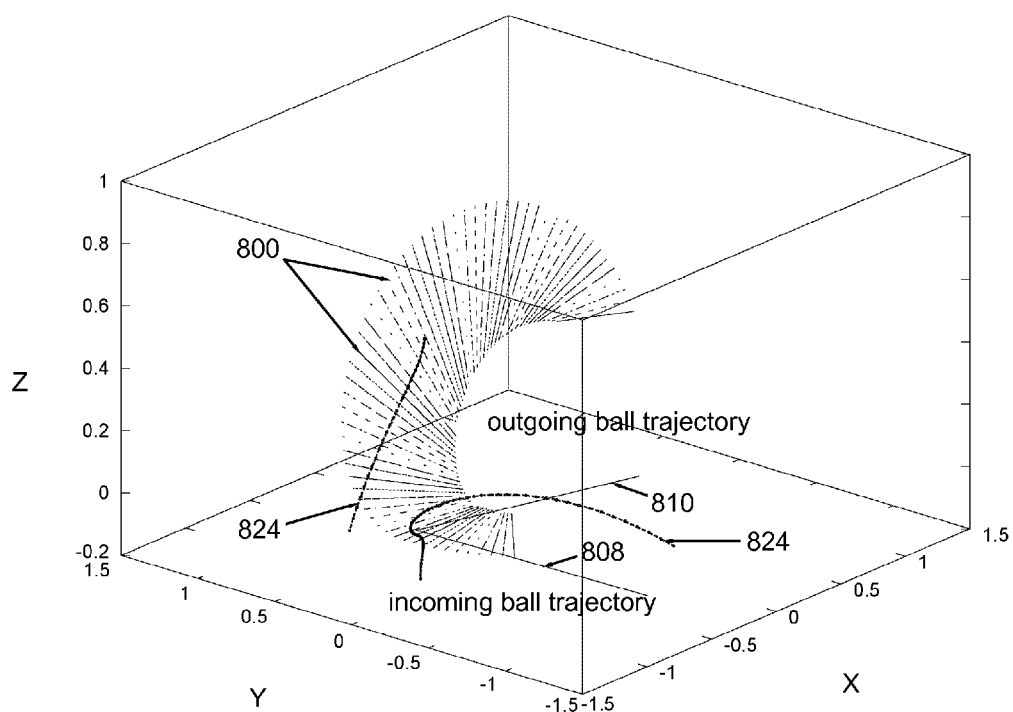
FIG. 33 is a three-dimensional (3D) plot illustrating bat swing, ball trajectory, and the feedback agreeing form as generated by the exemplary movement assessment software code described herein.
Figure 34:
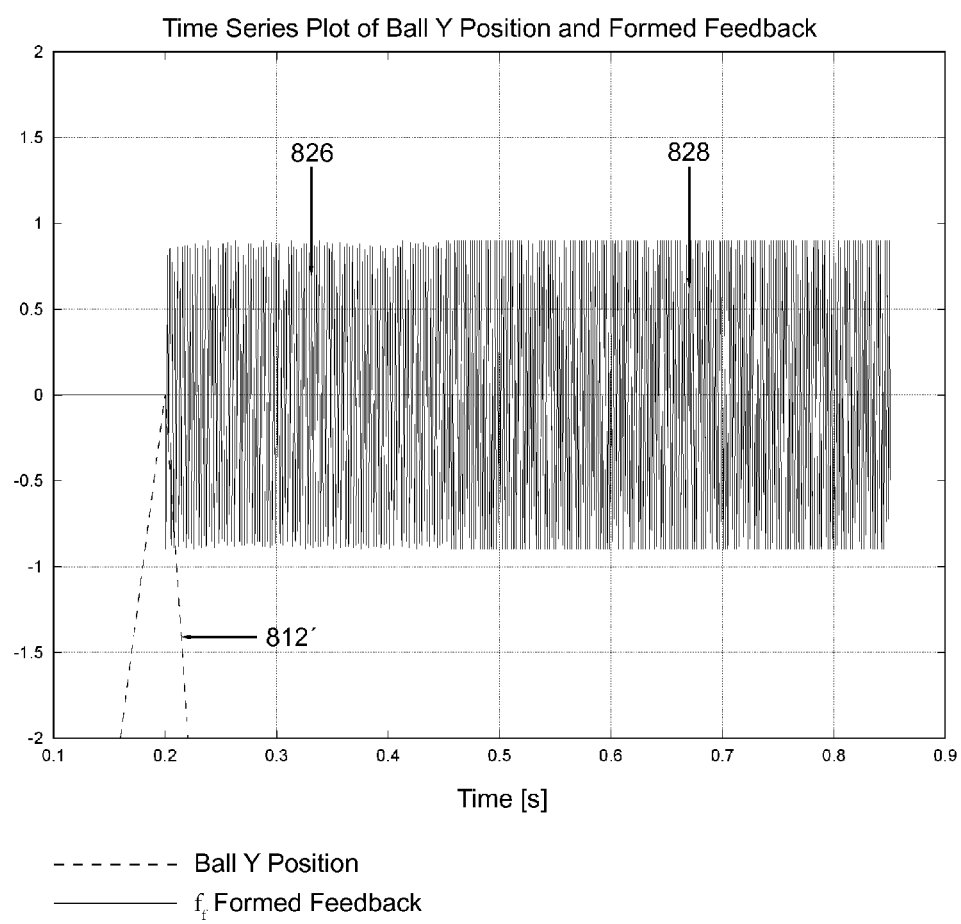
FIG. 34 is a time series plot illustrating ball Y position and formed feedback as generated by the exemplary movement assessment software code described herein.
Figure 35:
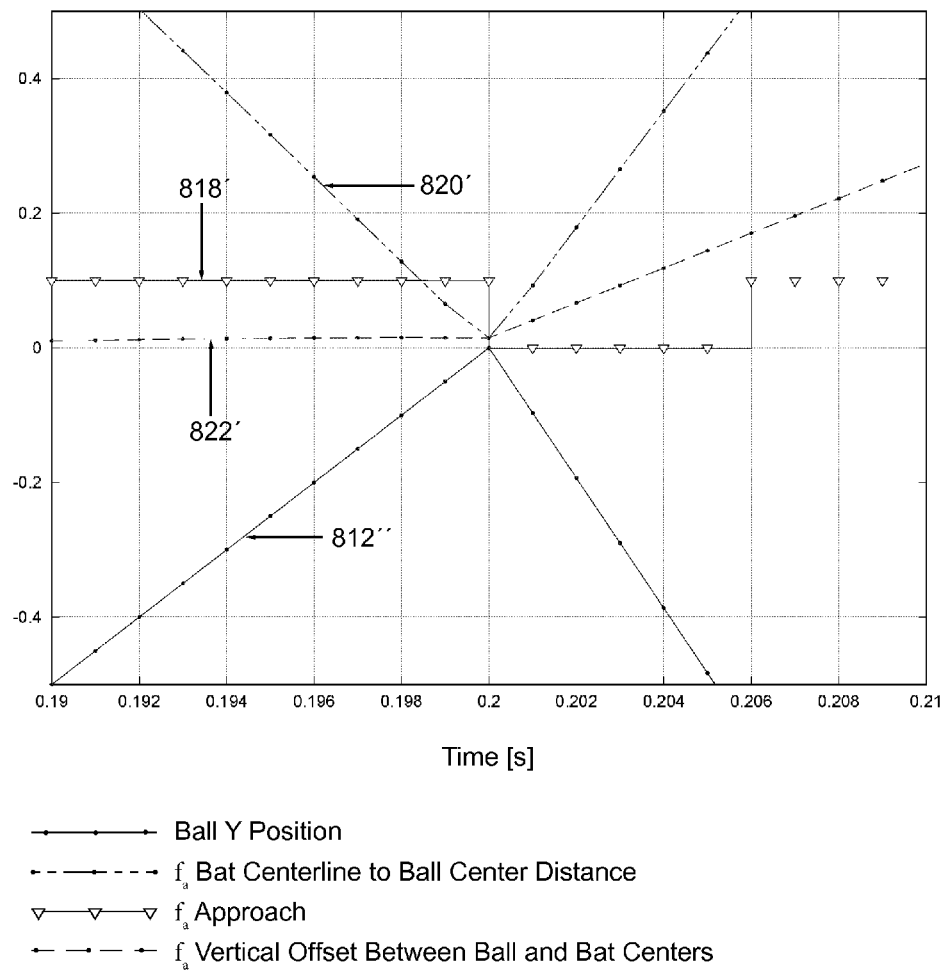
FIG. 35 is an enlarged view of a portion of FIG. 32, which illustrates the ball Y position and abstract feedback around the time of contact as generated by the exemplary movement assessment software code described herein.

In FIG. 33, the bat swing trajectory and the ball trajectory are illustrated together with curves depicting the feedback agreeing form 824. The feedback agreeing form 824 of the motion is the position of a point on the bat centerline that is closest to the bat. A time series plot of the ball y-position 812' and the formed feedback signal is illustrated in FIG. 34. The formed feedback is the monaural audio signal that is provided as a feedback to the batter. As shown in FIG. 34, the formed feedback signal comprises a two-tone melody comprising a first reference tone 826 and a second feedback tone 828. Finally, FIG. 35 illustrates a ball y-position curve 812", the feedback signal approach 818', the abstract feedback bat centerline to ball center distance curve 820', and a curve 822' illustrating the vertical offset between ball and bat centers, around the time in which the bat contacts the ball (i.e., FIG. 35 is an enlarged view of a portion of FIG. 32 around the time in which the bat contacts the ball).

Figure 19:
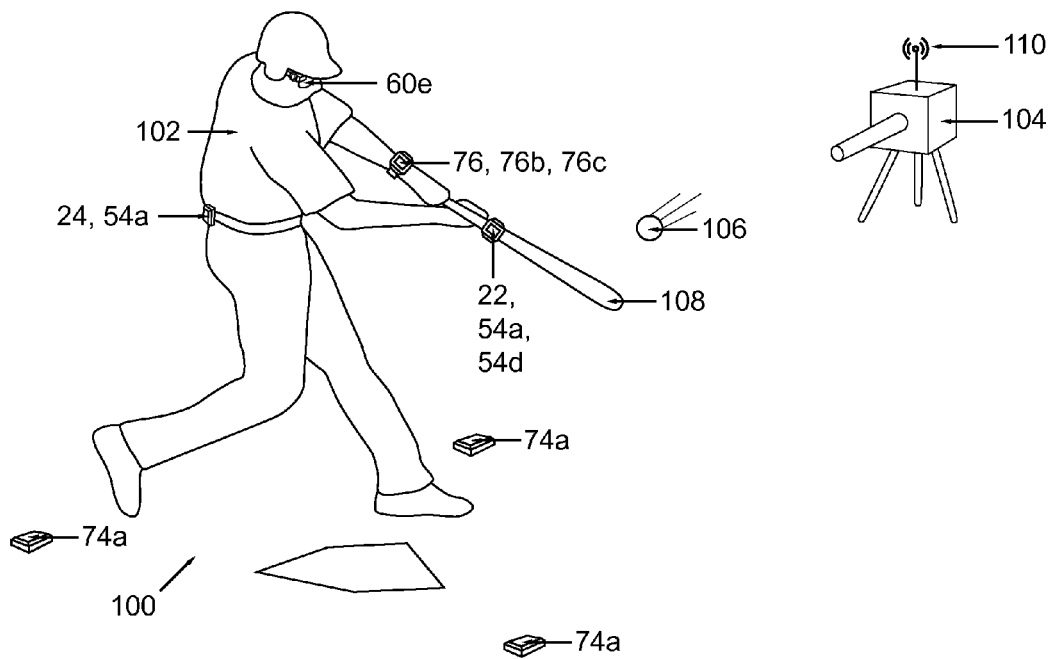
FIG. 19 is a diagrammatic perspective view of a first exemplary scenario wherein the movement assessment system described herein is being used to assess the athletic performance of a baseball player.

Now, with reference to FIGS. 19-25, various exemplary scenarios in which the movement assessment system 10 may be utilized to assess athletic performance will be described. For example, as shown in FIG. 19, the movement assessment system 10 described herein may be used to assess the athletic performance of a baseball player 102 that is hitting baseballs 106 being dispensed by an automatic baseball machine 104. In this scenario 100, a plurality of motion tracker reference light sources 74a are provided on the ground surrounding the baseball player 102. The bat 108, which is held by the baseball player 102, is provided with one or more sensor units 22 that at least include an inertial sensor 54a and a motion tracking sensor 54d. Also, the baseball player 102 is provided with a central control unit 24 on his torso (e.g., mounted on a waistband) that at least includes an inertial sensor 54a. In addition, the baseball player 102 is provided with a wearable visual display 60e or a wearable computing device having an optical head-mounted display (OHMD), such as Google® Glass™, for providing visual feedback to the player 102 on his or her performance. Referring again to FIG. 19, it can be seen that the arm of the baseball player 102 that is not holding the bat 108 is provided with a user interface device 76 having at least a display 76b and a touch input 76c for controlling the settings of the movement assessment system 10 (e.g., a mobile digital device, such as a smartphone mounted on an armband). The automatic ball machine 104 contains a wireless data interface 110 that enables the ball machine 104 to be controlled by the central control unit 24 worn by the baseball player 102 (e.g., the player 102 is able to adjust the settings of the ball machine 104 by using the user interface device 76, which is operatively coupled to the central control unit 24). In this scenario, the movement assessment system 10 is also preferably provided with one or more safety functions that automatically regulate the operation of the baseball machine 104 in the event of an emergency or accident (e.g., when the baseball player 102 has fallen on the ground, the dispensing of baseballs 106 from the baseball machine 104 is automatically stopped).

Another exemplary scenario in which the movement assessment system 10 may be utilized to assess athletic performance is illustrated in FIG. 20. In this scenario 200, the movement assessment system 10 is used to assess the athletic performance of a downhill skier 202. The boots 204 of the skier 202 are coupled to the respective skis 206 by virtue of bindings 208 with sensor units 22 incorporated therein. That is, each of the bindings 208 is provided with a sensor unit 22 having at least an inertial sensor 54a and a load sensor 54c. Also, as shown in FIG. 20, each of the ski poles 210 is provided with a sensor unit 22 having at least an inertial sensor 54a. The skier 202 is provided with a central control unit 24 on his torso (e.g., mounted on a waistband) that may include one or more additional sensors, such as an inertial sensor 54a, etc. As such, the performance of the skier 202 can be analyzed by the movement assessment system 10 during a downhill run or while the skier 202 traverses a cross-country ski course.

In FIGS. 21A and 21B, yet another exemplary scenario in which the movement assessment system 10 may be utilized to assess athletic performance is shown. In this scenario 300, the movement assessment system 10 is used to assess the athletic performance of a golfer 302 as he or she strikes a golf ball 306 with a golf club 304. The head 304a of the golf club 304 is provided with one or more sensor units 22 that at least include an inertial sensor 54a and a motion tracking sensor 54d. Also, the golfer 302 is provided with a central control unit 24 on his torso (e.g., mounted on a waistband) that at least includes an inertial sensor 54a. As shown in FIG. 21A, the golf ball 306 is disposed on a golf tee 308, which is provided with a motion tracking reference on the shaft thereof, such as a motion tracker reference light source 74a, a motion tracker reference magnetic signal 74b, and/or a motion tracker reference ultrasonic signal 74c. In addition, as best illustrated in FIG. 21B, the golf ball 306 is provided with a plurality of motion tracker reference light sources 74a dispersed throughout such that some subset of lights are always visible to the motion tracking sensor 54d on the golf club head 304a. As such, the golf club 304 is designed to track the golf ball 306 as it comes into proximity with the golf club head 304a. In FIG. 21A, it can be seen that the golfer 302 is additionally provided with a sensor unit 22 on his or her upper torso (e.g., on the upper chest) having at least an inertial sensor 54a for detecting the upper body movement of the golfer 302 as he or she strikes the ball 306. Thus, in the scenario 300, the performance of the golfer 302 may be analyzed by the movement assessment system 10.

Figure 22:
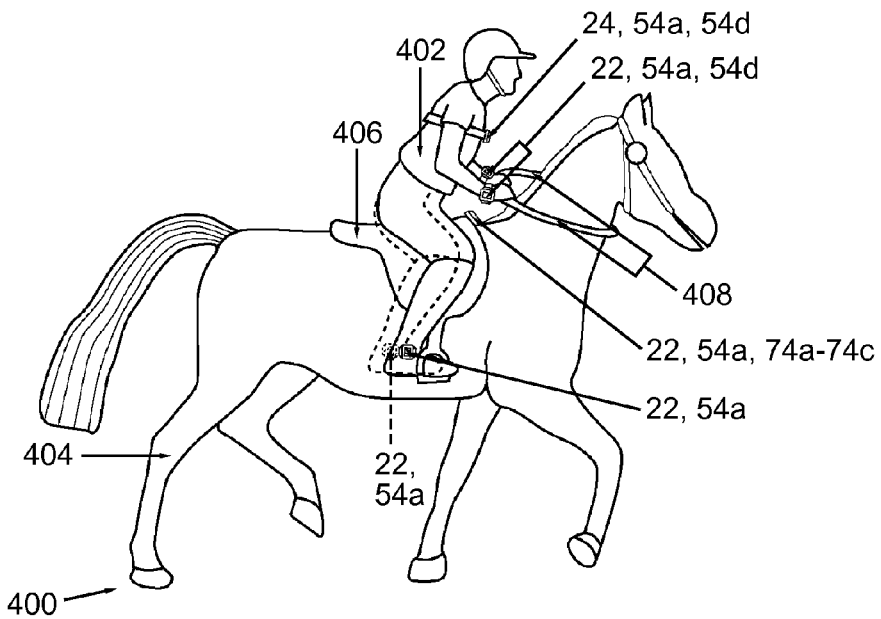
FIG. 22 is a diagrammatic perspective view of a fourth exemplary scenario wherein the movement assessment system described herein is being used to assess the athletic performance of a horseback rider.

In FIG. 22, still another exemplary scenario in which the movement assessment system 10 may be utilized to assess athletic performance is shown. In this scenario 400, the movement assessment system 10 is used to assess the athletic performance of a horseback rider 402 as he or she is riding a horse 404. For the example, the horseback rider 402 may be a jockey and the horse 404 may be a race horse. In such a scenario, the movement assessment system 10 is used to assess the performance of the jockey as he or she rides the horse during a race. As shown in FIG. 22, the saddle 406 disposed on the horse 404 is provided with one or more sensor units 22 that at least include an inertial sensor 54a. Also, the saddle 406 is provided with a motion tracking reference disposed thereon, such as a motion tracker reference light source 74a, a motion tracker reference magnetic signal 74b, and/or a motion tracker reference ultrasonic signal 74c. In addition, the horseback rider 402 is provided with a central control unit 24 on his torso (e.g., mounted on a band) that at least includes an inertial sensor 54a and a motion tracking sensor 54d. Each wrist of the horseback rider 402 is provided with one or more respective sensor units 22 disposed thereon (e.g., mounted on a wristband), which each at least include an inertial sensor 54a and a motion tracking sensor 54d. In one or more embodiments, the one or more sensor units 22, which are disposed on each of the wrists of the horseback rider 402, detect the motion of the wrists of the horseback rider 402 as he or she manipulates the reins 408. In FIG. 22, it can be seen that each ankle of the horseback rider 402 is additionally provided with one or more sensor units 22 disposed thereon (e.g., mounted on ankle bands). Each of the one or more sensor units 22 at least includes an inertial sensor 54a for detecting the motion of the legs of the horseback rider 402 as he or she is riding the horse 404.

Figure 23:
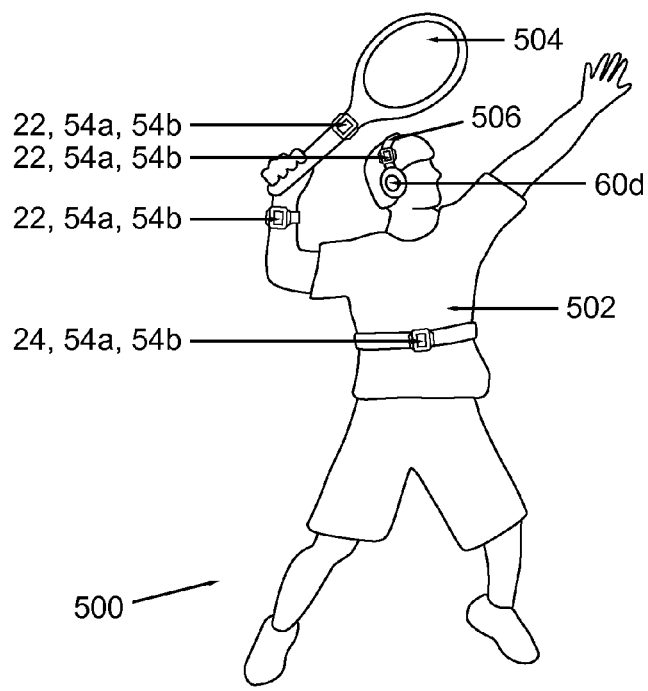
FIG. 23 is a diagrammatic perspective view of a fifth exemplary scenario wherein the movement assessment system described herein is being used to assess the athletic performance of a tennis player.

In FIG. 23, yet another exemplary scenario in which the movement assessment system 10 may be utilized to assess athletic performance is shown. In this scenario 500, the movement assessment system 10 is used to assess the athletic performance of a tennis player 502 as he or she is hitting tennis balls with a tennis racket 504. The tennis player 502 is provided with a central control unit 24 on his torso (e.g., mounted on a waistband) that at least includes an inertial sensor 54a and a magnetometer-type sensor 54b. The central control unit 24 on the torso of the tennis player 502 may also include a wireless data interface 62' (e.g., in the form of Bluetooth), a wired data interface 64' for data maintenance and/or charging (e.g., in the form of a USB connection), a power source in the form of a battery 66', a wireless power receiver 68' for charging the battery 66' of the central control unit 24, nonvolatile memory 72', and user interfaces 76' in the forms of one or more buttons 76a and a display 76b. The handle or throat of the tennis racket 504, which is held by the tennis player 502, is provided with one or more sensor units 22 that at least include an inertial sensor 54a and a magnetometer-type sensor 54b. Also, the wrist of the tennis player 502 holding the racket is provided with one or more sensor units 22 (e.g., mounted on a wristband) that also at least include an inertial sensor 54a and a magnetometer-type sensor 54b. In addition, one or more sensor units 22, which at least include an inertial sensor 54a and a magnetometer-type sensor 54b, are mounted on the headphones 506 of the tennis player 502. The one or more sensor units 22 on the tennis racket 504, the wrist of the tennis player 502, and the headphones 506 of the tennis player 502 may also include a wireless data interface 62 (e.g., in the form of Bluetooth) for communicating with the central control unit 24, a power source in the form of a battery 66, and basic user interfaces 76 comprising one or more buttons 76a and a simple display 76b. In addition to the one or more sensor units 22, the headphones 506 worn by the tennis player 502 also include a wireless data interface 62 (e.g., in the form of Bluetooth) for communicating with the central control unit 24, a power source in the form of a battery 66, and an auditory sensory output device 60d (i.e., the headphones 506 may comprise stereo speakers for providing auditory biofeedback to the tennis player 502 as he or she is hitting tennis balls). In one or more embodiments, the headphones 506 are in the form of Bluetooth headphones.

Figure 24:
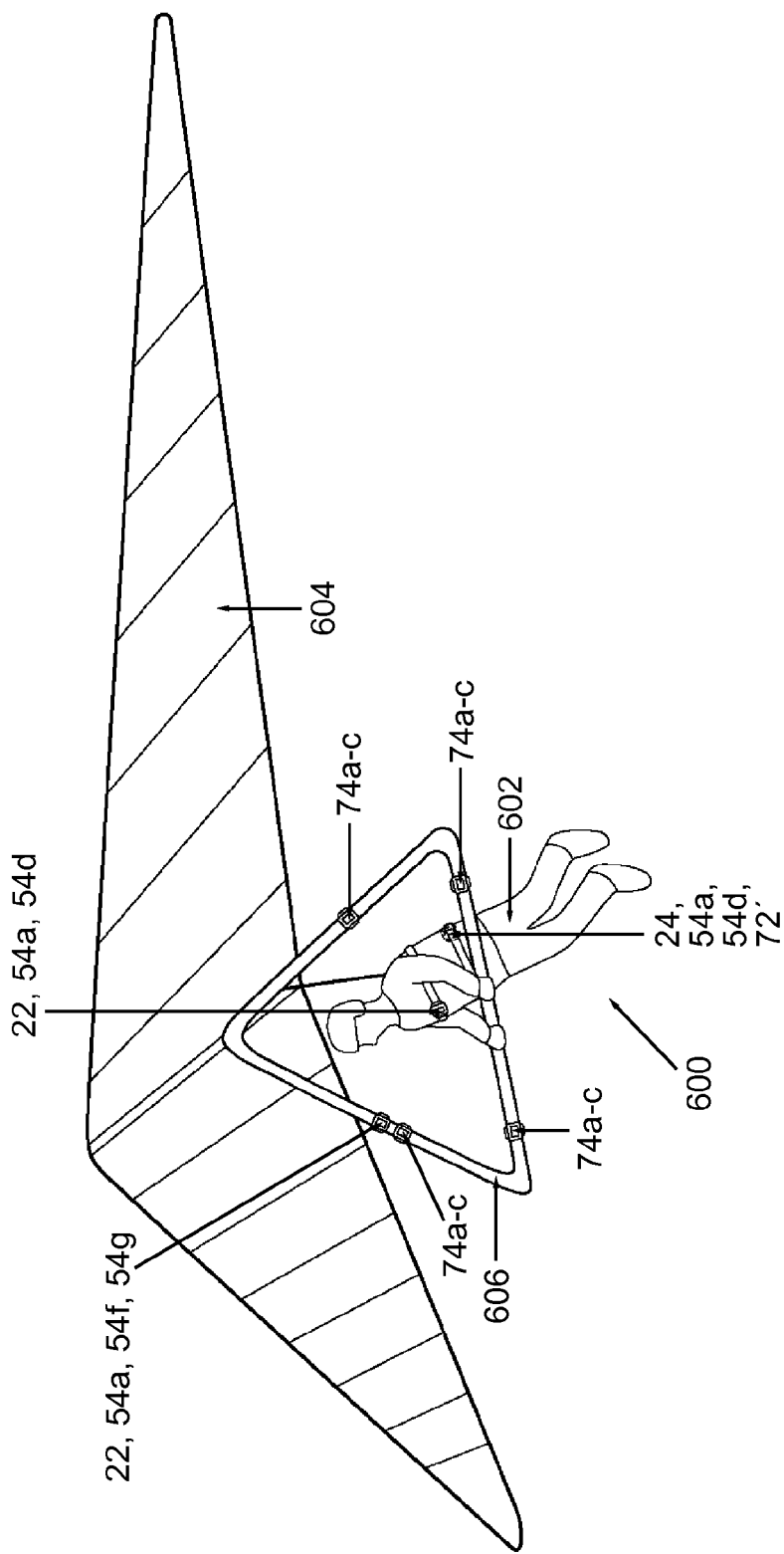
FIG. 24 is a diagrammatic perspective view of a sixth exemplary scenario wherein the movement assessment system described herein is being used to assess the athletic performance of a handglider.

In FIG. 24, still another exemplary scenario in which the movement assessment system 10 may be utilized to assess athletic performance is shown. In this scenario 600, the movement assessment system 10 is used to assess the performance of a person 602 as he or she is flying a handglider 604. As shown in this figure, the handle bar assembly 606 of the handglider 604 is provided with a plurality of motion tracking reference devices thereon, which may be in the form of motion tracker reference light sources 74a, motion tracker reference magnetic signals 74b, and/or motion tracker reference ultrasonic signals 74c. In addition, the handle bar assembly 606 of the handglider 604 is provided with a sensor unit 22 attached thereto, wherein the sensor unit 22 comprises at least an inertial sensor 54a, an air pressure sensor 54f for detecting the atmospheric air pressure, and a global positioning system ("GPS") sensor 54g for detecting the location of the handglider 604. Referring again to FIG. 24, it can be seen that the person 602 flying the handglider 604 is provided with a central control unit 24 on his or her torso (e.g., mounted on a waistband) that at least includes an inertial sensor 54a and a motion tracking sensor 54d. The central control unit 24 on the torso of the person 602 also includes at least non-volatile memory 72' for storing data the measurement data acquired by the plurality of sensing devices (e.g., 54a, 54d). The person 602 on the handglider 604 is additionally provided with a sensor unit 22 on his or her upper torso (e.g., on the upper chest) also having at least an inertial sensor 54a for detecting the upper body movement of the person 602 and a motion tracking sensor 54d for tracking the motion of the upper body of the person 602.

Figure 25:
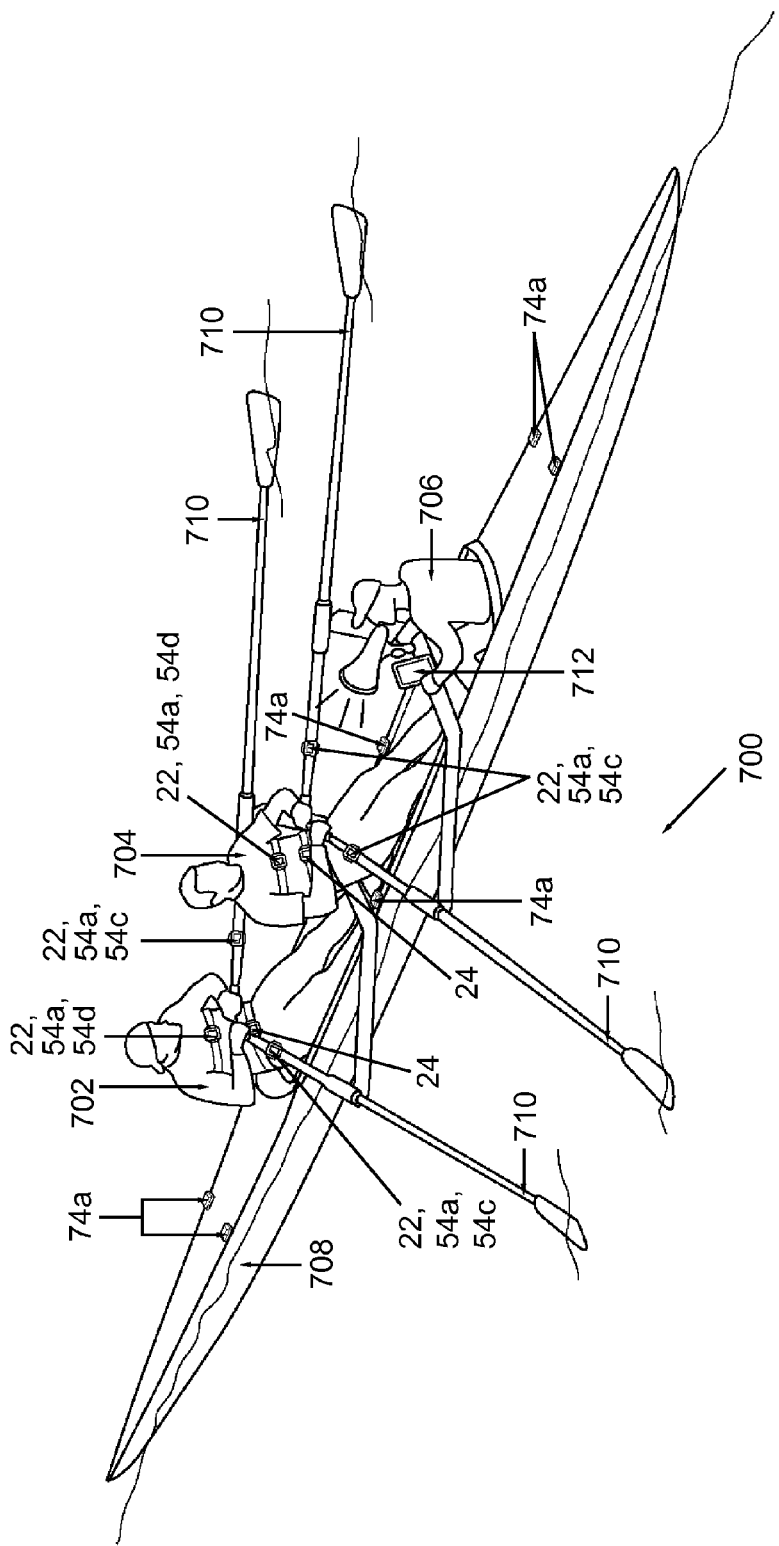
FIG. 25 is a diagrammatic perspective view of a seventh exemplary scenario wherein the movement assessment system described herein is being used to assess the athletic performance of a rowing team.

In FIG. 25, yet another exemplary scenario in which the movement assessment system 10 may be utilized to assess athletic performance is shown. In this scenario 700, the movement assessment system 10 is used to assess the athletic performance of a plurality of members 702, 704 of a rowing team that are propelling a row boat 708 using oars 710 disposed on opposite sides of the row boat 708. As shown in this figure, the row boat 708 is provided with a plurality of motion tracker reference light sources 74a disposed on the upper surface thereof dispersed throughout such that some subset of lights is always visible to the motion tracking sensors 54d disposed on the rowing team members 702, 704. In an exemplary embodiment, each of the reference light sources 74a includes a battery 66 and a wireless power receiver 68 for supplying the light emitting devices (e.g., light emitting diodes or LEDs) of the reference light sources 74a with power. While a total of six (6) motion tracker reference light sources 74a are shown on the upper surface of the row boat 708 in FIG. 25, it is to be understood that any suitable quantity of reference light sources 74a may be used as long as at least some of the reference light sources 74a are visible to the motion tracking sensors 54d.

With reference again to FIG. 25, it can be seen that each of the oars 710 is provided with a sensor unit 22 disposed thereon. Each of the sensor units 22 includes at least an inertial sensor 54a and a load sensor 54c for measuring the oar loading. Also, each oar sensor unit 22 may comprise a power source in the form of a battery 66, a wireless power receiver 68 for charging the battery 66 of the sensor unit 22, non-volatile memory 72 for storing data the measurement data acquired by the plurality of sensing devices (e.g., 54a, 54c), a wireless data interface 62 (e.g., in the form of Bluetooth) for communicating with the central control unit 24 on each respective rower 702, 704, and a user interface 76 in the form of a display 76b. As shown in FIG. 25, each rower 702, 704 is provided with a central control unit 24 that includes a wireless data interface 62' in the form of Bluetooth and Wi-Fi (i.e., wireless local area networks). Each rower 702, 704 is additionally provided with a sensor unit 22 on his upper torso (i.e., on the upper chest) also having at least an inertial sensor 54a for detecting the upper body movement of the rower 702, 704 and a motion tracking sensor 54d for tracking the motion of the upper body of the rower 702, 704. Each upper torso sensor unit 22 may also comprise at least a power source in the form of a battery 66, a wireless power receiver 68 for charging the battery 66 of the sensor unit 22, and a wireless data interface 62 (e.g., in the form of Bluetooth) for communicating with the central control unit 24 on each respective rower 702, 704, and a user interface 76 in the form of a display 76b. In one or more embodiments, the sensor units 22 on the oars 710 held by the first rowing team member 702 wirelessly communicate with the central control unit 24 disposed on the first rowing team member 702 by means of Bluetooth. The upper torso sensor unit 22 on the first rowing team member 702 also communicates with the central control unit 24 disposed on the first rowing team member 702 by means of Bluetooth. Similarly, the sensor units 22 on the oars 710 held by the second rowing team member 704, and the upper torso sensor unit 22 on the second rowing team member 704, wirelessly communicate with the central control unit 24 disposed on the second rowing team member 704 by means of Bluetooth. Each of the central control units 24 that are disposed on the first and second rowing team members 702, 704 wirelessly communicate with the tablet 712 held by the rowing team instructor or captain 706 by Wi-Fi. As such, the rowing team instructor or captain 706 is able to continually monitor the performance of the rowing team members 702, 704 as they are propelling the row boat 708 on a body of water, such as a river, lake, or reservoir. Also, the tablet 712 may comprise a touchscreen-type user interface with a graphic-based keypad or graphic-based keyboard that enables the instructor or captain 706 to input commands using the tablet 712, and/or one or more graphic-based selection buttons or knobs that enable the instructor or captain 706 to make various mode selections for the movement assessment system (i.e., to select a particular activity for analysis and/or to select particular aspects of a certain activity for analysis).

In addition for being used to analyze athletic performance, it is to be understood that the movement assessment apparatus or system 10 described herein may also be utilized to analyze the balance and gait of an individual undergoing rehabilitation. For example, suppose an individual sustained an injury that has adversely affected his or her balance, the movement assessment apparatus or system 10 described herein may be used to assess the progress of his or her rehabilitation.

As one example of a rehabilitative application, in some embodiments, the movement assessment apparatus or system 10, which is shown in FIGS. 1 and 2, is used to determine positional data (i.e., three-dimensional coordinates) and/or a velocity profile for one or more body gestures of the subject or patient during the performance of a task of daily living. The one or more body gestures of the subject or patient may comprise at least one of: (i) one or more limb movements of the patient, (ii) one or more torso movements of the patient, and (iii) a combination of one or more limb movements and one or more torso movements of the patient. For example, one such task of daily living may comprise a scenario wherein a patent is walking along a prescribed path (e.g., a straight-line extending a predetermined distance). While the patient is performing this task of daily living, the movement assessment apparatus 10 may analyze the performance of the patient during the execution of this task, and then provide appropriate real-time feedback to the patient regarding his or her performance. In particular, one or more sensor units 22 of the movement assessment apparatus 10 may be coupled to each of the patient's legs such that the motion of the patient's legs may be detected. Then, the data processing device (e.g., 52, 52') of the movement assessment apparatus 10 may be used to determine the movement paths or velocity profiles for each of the patient's legs by using the output signals of the one or more sensor units 22. After which, the data processing device (e.g., 52, 52') of the movement assessment apparatus 10 may compare the movement paths and/or the velocity profiles determined for each of the patient's legs to respective baseline movement paths and/or velocity profiles (e.g., to baseline movement paths or baseline velocity profiles for an individual having a normal gait pattern) and determine how closely the movement paths and/or the velocity profiles determined for the legs of the patient conform to the respective baseline movement paths and/or baseline velocity profiles. After performing the comparison of the movement paths and/or the velocity profiles determined for each of the patient's legs to respective baseline movement paths and/or velocity profiles, the data processing device (e.g., 52, 52') of the movement assessment apparatus 10 generates a sensory output signal based upon the conformity of the movement paths and/or velocity profiles for each of the patient's legs to the respective baseline movement paths and/or velocity profiles so that the appropriate biofeedback may be delivered to the patient. As such, based upon a comparison of the patient's actual leg movement paths and/or velocity profiles to the baseline movement paths and/or velocity profiles, a physical therapist treating the subject or patient may conclude that the subject's condition is improving over time. Thus, advantageously, the movement assessment apparatus or system 10 enables a subject's movement to be analyzed during a task of daily living so that a determination can be made as to whether or not the subject's gait is improving.

Although the invention has been shown and described with respect to a certain embodiment or embodiments, it is apparent that this invention can be embodied in many different forms and that many other modifications and variations are possible without departing from the spirit and scope of this invention. Moreover, while reference is made throughout this disclosure to, for example, "an illustrative embodiment", "an exemplary embodiment", "one embodiment" or a "further embodiment", it is to be understood that some or all aspects of these various embodiments may be combined with another as part of an overall embodiment of the invention.

In addition, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

Exemplary Source Code

The exemplary source code provided below generates a simulated executed motion for softball batting, and provides audible feedback for the vertical location of the bat-on-ball. The feedback is provided after the bat has contacted the ball. While the exemplary source code is written particularly for Octave 3.6 (see http://octave.sf.net), it is to be understood that this source code can be readily adapted for other computer programming languages.

In the exemplary code, the executed motion is the position of the center of the ball, and the position of two points on the centerline of the bat. The reference motion is the ball center position taken directly from the executed motion. The feedback-agreeing form is the position of a point on the bat centerline closest to the ball.

In the exemplary code provided below, the abstract feedback comprises the following elements: (1) instantaneous closest distance between bat centerline and ball center, (2) an approach flag, which is set true when the ball distance is decreasing, and which is set false when the distance is increasing after a strike or miss, and (3) a vertical component of the distance between the bat centerline and the ball center.

The formed feedback generated by the exemplary code comprises a two tone melody, starting after the approach flag turns false. The first tone is a reference tone, the second tone is higher or lower compared to the reference depending on how high or low the hit was with relation to the center of the ball. The first tone lasts 250 ms, the second tone lasts 400 ms.

In the exemplary code provided below, a right-handed coordinate system is utilized, wherein the z axis points straight up, and the x and y axes are in the horizontal plane. At the point of contact, z=0, solely for convenience in simulating the motion capture. All measurements in the exemplary code are in SI units (meters, seconds, etc.).

The exemplary source code is as follows:

```
%
% Example of Feedback Generation
% Batting Contact Location, dated 06/19/2014
% written for Octave 3.6, see http://octave.sf.net
%
% Activity: softball batting
% All positions are 3D in ground reference frame unless
stated otherwise.
% Executed Motion: position of the center of the ball,
position of two points
% on the centerline of the bat.
% Reference Motion: ball center position taken directly
from the executed motion.
% Feedback-agreeing form:
% Position of a point on the bat centerline closest to
the ball.
% Abstract Feedback:
% 1. Instantaneous closest distance between bat
centerline and ball center.
% 2. Approach flag: true when the ball distance is
decreasing, false when the
%     distance is increasing after a strike or miss.
% 3. Vertical component of the distance between the bat
centerline and the ball
%     center.
% Formed Feedback:
% A two tone melody, starting after the approach flag
turns false. The first
% tone is a reference tone, the second tone is higher or
lower compared to
% the reference depending on how high/low the hit was
with relation to the
% center of the ball. First tone lasts 250ms, second tone
lasts 400ms.
%
% Coordinate system: Right-handed system, z points
straight up, x and y are
% in the horizontal plane. z=0 is at the point of
contact, solely for
% convenience in simulating the motion capture.
%
% All measurements are in SI units (metres, seconds).
setenv GNUTERM qt
pkg load linear-algebra geometry audio signal
global deg = pi/180; % One degree of angle in radians
global sound play utility='/opt/local/bin/play -q -t AU -
';
global f_factor = 16;
% The formed feedback is sampled at 16 times the sampling
rate
% of the motion, since its frequency content is much
higher
% than that of the motion.
%% Simulate an Executed Motion
global p_i p_o p_o_unit
function p=bat(t)
    global deg
    bat_in = [-0.5 0 0]'; % inner point on the bat
    bat_out = [-1.1 0 0]'; % outer point on the bat
    bat_in_sweep = 100*deg; % sweep angle of inner bat
point
    bat_out_sweep = 160*deg; % sweep angle of outer bat
point
    swing_incl = -90*deg; % initial inclination of the
swing plane
    N = length(t);
    t(t < 0) = 0;
    t(t > 1.2) = 1.2;
    t1 = t;
    t1 (t1 > 1) = 1;
    bat_in_angle = (1-t).*bat_in_sweep;
    bat_out_angle = (1-t).*bat_out_sweep;
    swing_incl = (1-t1)*swing_incl;
    axis = reshape(rotv([1 0 0], swing_incl)*[0 0 1]', 3,
N);
    global p_i p_o p_o_unit
    p_i = reshape(rotv(axis', bat_in_angle)*bat_in, 3,
N);
```

```
p_o = reshape(rotv(axis', bat_out_angle)*bat_out, 3,
N);
p_o_unit = (p_o-p_i).*([1 1 1]'*(1./norm(p_o-p_i,
'columns')));
p_o = p_i + p_o_unit * norm(bat_out - bat_in);
p = [p_i; p_o];
end
function p=ball(t)
    global deg
    ball_offset = [0 0 .015]'; % contact point offset
    x_incl_in = 0.5*deg; % incoming inclination
    x_incl_out = 15*deg; % outgoing inclination
    v_in = 10; % incoming velocity
    v_out = 20; % outgoing velocity
    N = length(t);
    t_in = t <= 1;
    t_out = t >= 1;
    p_in = (rotv([1 0 0], x_incl_in)*[0 -1
0]')*(t_in.*(1-t)*v_in);
    p_out = (rotv([1 0 0], x_incl_out)*[0 -1
0]')*(t_out.*(t-1)*v_out);
    p = p_in + p_out + [-1 0 0]' + ball_offset;
end
T = 0.2; % Assume a swing lasts 0.2s from the highest
point to contact
global tau = 1/1000; % Sample at 1000Hz
t = -0.3:(tau/T):1.5; % A parameter that goes from 0 to 1
over the duration of
                                % the swing. This is *not* time. It
is sampled at the
                                % sampling frequency.
p = [bat(t); ball(t)]';
%%% Calculate Reference Motion
w = p(:, 7:9);
%%% Calculate Feedback Agreeing Form
function pa = gen_pa(p)
    bat1 = p(:, 1:3);
    bat2 = p(:, 4:6);
    ball = p(:, 7:9);
    % A plane normal to the bat, passing through the
ball.
    normal = bat2-bat1;
    plane = createPlane(ball, normal);
    % The intersection of the plane and the bat is the
point closest to the ball
    pa = intersectLinePlane([bat1 normal], plane);
end
pa = gen_pa(p);
%%% Calculate Abstract Feedback
function fa = gen_fa(pa, w)
    % Instantaneous closest distance between bat
centerline and ball center.
    bat_ball = distancePoints(pa, w, 'diag');
    % True when the ball distance is decreasing, false
when the
    % distance is increasing after a strike or miss. The
value is locked out
    % at true when the distance from bat midpoint to the
ball exceeds 0.5m.
    approach = [1; (bat_ball(2:end) <= bat_ball(1:end-1))
| (bat_ball(2:end) > 0.5)];
    % Vertical component of the distance between the bat
centerline and the ball
    % center.
    vert = w(:,3) -pa(:,3);
    fa = [bat_ball approach vert];
end
fa = gen_fa(pa, w);
%%% Calculate Formed Feedback
function ff = gen_ff(fa)
    global tau f_factor
    ftau = tau/f_factor;
    T1 = 0.25; % duration of the reference tone
    f1 = 440; % frequency of the reference tone
    T2 = 0.4; % duration of the feedback tone
    sens = 40/0.01; % feedback sensitivity in Hz/m of
displacement
    % Index at which the formed feedback should start
    start_idx = (find(!fa(:,2))(1) - 1) * f_factor;
    ff = zeros(start_idx + (T1+T2)/ftau, 1);
    f2 = f1 + sens * fa(start_idx/f_factor, 3); %
frequency of the feedback tone
    if f2 < 50
        f2 = 50;
    end
    N1 = T1 * f1; % number of periods of the reference
tone
    n1 = floor(T1 / ftau); % number of samples of the
reference tone
    N2 = T2 * f2; % number of periods of the feedback
tone
    n2 = floor(T2 / ftau); % number of samples of the
feedback tone
    ff(start_idx:start_idx+n1) =
0.9*sawtooth(0:(2*pi*N1)/n1:(2*pi*N1), 0.5);
    ff(start_idx+n1:start_idx+n2) =
0.9*sawtooth(0:(2*pi*N2)/n2:(2*pi*N2), 0.5);
end
ff = gen_ff(fa);
%%% Utilities
%
function plot3d(varargin)
    args = { };
    for i = 1:length(varargin)
        arg = varargin{i};
        if (ismatrix(arg) && !ischar(arg) &&
!isscalar(arg))
            args = {args{:}, arg(1:3:end,:),
arg(2:3:end,:), arg(3:3:end,:)};
        else
            args = {args{:}, arg};
        end
    end
    plot3(args{:});
end
%%% Generate Plots
%
for i=0:1
    f=figure;
    c=get (f, 'colormap');
    set(f, 'colormap', c*0);
    plot3d(p(1:4:end, 1:6)', p(:, 7:9)', '-');
    axis([-1.5 1.5 -1.5 1.5 -0.2 1])
    view(-50, 30);
    set(get(f, 'children'), 'fontname', 'Helvetica');
    if (i)
        xlabel 'X'
        ylabel 'Y'
        zlabel 'Z'
        title 'Oblique View of the Bat Swing and Ball
Trajectory'
        text(-.5, .55, -.35, 'incoming ball trajectory')
        text(0.7, .9, -.18, 'outgoing ball trajectory')
        print plot1ann.pdf
    else
        print -mono plot1.pdf
    end
end
for i=0:1
    f=figure;
    plot(p(1:4:end, [2 5])', p(1:4:end, [3 6])', 'k',
        p(1:4:end, 8), p(1:4:end, 9), 'k-.');
    set(gca( ), 'xdir', 'reverse');
    axis([-0.5 1.2 -0.2 1])
    axis square equal
    grid on
    set(get(f, 'children'), 'fontname', 'Helvetica');
    if (i)
        xlabel 'Y'
        ylabel 'Z'
        text(-.1, .15, 'outgoing ball trajectory')
        text(-.1, -.05, 'incoming ball trajectory')
        title 'YZ plane view of the bat swing and ball
trajectory'
        print plot2ann.pdf
    else
        print plot2.pdf
    end
end
```

```
end
for i=0:1
    f=figure;
    plot(p(1:4:end, [1 4])', p(1:4:end, [2 5])', 'k',
       p(1:4:end, 7), p(1:4:end, 8), 'k-.');
    axis([-1.3 1.7 -1.2 1.3])
    axis square equal
    grid on
    set(get(f, 'children'), 'fontname', 'Helvetica');
    if (i)
        xlabel 'X'
        ylabel 'Y'
        text(-.95, -1, 'ball trajectory')
        title 'XY plane view of the bat swing and ball
trajectory'
        print -solid -mono plot3ann.pdf
    else
        print plot3.pdf
    end
end
for i=0:1
    f=figure;
    plot(t*T, p(:,8), t*T, fa(:,1), t*T, fa(:,2), t*T,
fa(:,3));
    axis([0 0.3 -10 10])
    grid on
    set(get(f, 'children'), 'fontname', 'Helvetica');
    if (i)
        legend('ball Y position', 'f_a bat centerline
to ball center distance',
            'f_a approach', 'f_a vertical offset between
ball and bat centers');
        xlabel 'time [s]';
        title 'Time series plot of ball Y position and
abstract feedback';
        print plot4ann.pdf
    else
        print plot4.pdf
    end
end
for i=0:1
    f=figure;
    plot3d(p(1:4:end,1:6)', p(:,7:9)', 'k-', pa(:,1:3)',
'ko', 'markersize', 0.75);
    axis([-1.5 1.5 -1.5 1.5 -0.2 1])
    view(-50,30);
    set(get(f, 'children'), 'fontname', 'Helvetica');
    if (i)
        xlabel 'X'
        ylabel 'Y'
        zlabel 'Z'
        text(-.5,.55,-.35,'incoming ball trajectory')
        text(0.7,.9,-.18,'outgoing ball trajectory')
        title(['Oblique View of the Bat Swing, Ball
Trajectory and the Feedback'
            ' Agreeing Form']);
        print plot5ann.pdf
    else
        print -mono -dashed plot5.pdf
    end
end
for i=0:1
    f=figure;
    t0=t(1)*T;
    plot(t*T, p(:,8), t0:tau/f_factor:t0+(rows(ff) -
1)*tau/f_factor, ff);
    axis([0.1 0.9 -2 2])
    grid on
    set(get(f, 'children'), 'fontname', 'Helvetica');
    if (i)
        legend('ball Y position', 'f_f formed
feedback');
        xlabel 'time [s]';
        title 'Time series plot of ball Y position and
formed feedback';
        print plot6ann.pdf
    else
        print -mono plot6.pdf
    end
end
for i=0:1
    f=figure;
    plot(t*T, p(:,8), '.-', t*T, fa(:,1), '.-', t*T,
0.1*fa(:,2), '<', t*T, fa(:,3), '.-');
    axis([0.19 0.21 -0.5 0.5])
    grid on
    set(get(f, 'children'), 'fontname', 'Helvetica');
    if (i)
        legend('ball Y position', 'f_a bat centerline
to ball center distance',
            'f_a approach', 'f_a vertical offset between
ball and bat centers');
        xlabel 'time [s]';
        title 'Time series plot of ball Y position and
abstract feedback';
        print plot7ann.pdf
    else
        print plot7.pdf
    end
end
```

The invention claimed is:

1. A movement assessment apparatus configured to provide biofeedback to a user regarding one or more movements executed by the user, the movement assessment apparatus comprising:

at least one sensing device, the at least one sensing device comprising one or more sensors for detecting the motion of a body portion of a user and/or the motion of an object manipulated by the user and outputting one or more signals that are generated based upon the motion of the body portion of the user and/or the motion of the object, the at least one sensing device further comprising attachment means for attaching the at least one sensing device to the body portion of the user or to the object manipulated by the user;

a data processing device operatively coupled to the at least one sensing device, the data processing device configured to receive the one or more signals that are output by the one or more sensors of the at least one sensing device, and to determine executed motion data of the body portion of the user and/or executed motion data of the object manipulated by the user using the one or more signals, the data processing device further configured to: (i) execute an agreement operation by converting the executed motion data to a feedback-agreeing form that agrees with at least one of the dimensions, reference frames, and units of baseline motion data of a reference motion, (ii) execute a comparison operation by comparing the feedback-agreeing form of the executed motion data to the baseline motion data of the reference motion, and (iii) determine how closely the feedback-agreeing form of the executed motion data conforms to the baseline motion data of the reference motion, the data processing device additionally configured to generate an abstract feedback signal based upon the execution of the comparison operation; and a sensory output device operatively coupled to the data processing device, the sensory output device configured to generate a formed feedback signal for delivery to the user that is based upon the abstract feedback signal, the formed feedback signal comprising at least one of a visual indicator, an audible indicator, and a tactile indicator, and the sensory output device further configured to output the at least one of the visual indicator, the audible indicator, and the tactile indicator to the user in order to provide biofeedback as to conformity of the executed motion data to the baseline motion data of the reference motion.

2. The movement assessment apparatus according to claim 1, wherein the one or more sensors of the at least one sensing device comprise at least one of: (i) an accelerometer, (ii) a gyroscope, and (iii) a magnetometer.

3. The movement assessment apparatus according to claim 1, wherein the at least one sensing device comprises a plurality of sensing devices, a first of the plurality of sensing devices configured to be attached to a limb of the user, a second of the plurality of sensing devices configured to be attached to a first torso location of the user, a third of the plurality of sensing devices configured to be attached to a head of the user, and a fourth of the plurality of sensing devices configured to be attached to a second torso location of the user.

4. The movement assessment apparatus according to claim 1, wherein the attachment means of the at least one sensing device comprises a resilient band for attaching the at least one sensing device to one of a limb of the user, a torso of the user, a head of the user, and an object manipulated by the user.

5. The movement assessment apparatus according to claim 1, wherein the data processing device comprises a microprocessor.

6. The movement assessment apparatus according to claim 1, wherein the at least one sensing device further comprises one or more additional sensors for detecting at least one of: (i) a position of the user, (ii) a body parameter of the user, and (iii) an environmental parameter.

7. The movement assessment apparatus according to claim 6, wherein the one or more additional sensors of the at least one sensing device comprise at least one of: (i) a global positioning system sensor for detecting a position of the user, (ii) a body oxygenation sensor for detecting an oxygen level or oxygen saturation level of the user, (iii) a body temperature sensor for detecting a body temperature of the user, (iv) an ambient temperature sensor for detecting a temperature of an environment in which the user is disposed, and (v) a humidity sensor for detecting a humidity level of the environment in which the user is disposed.

8. The movement assessment apparatus according to claim 1, wherein the one or more sensors of the at least one sensing device are configured to detect the motion of an object manipulated by the user, and wherein the object manipulated by the user comprises one of: (i) a golf club, (ii) a baseball bat or softball bat, (iii) a tennis racket, (iv) an oar for rowing a boat, (v) a ski, (vi) a ski pole, and (vii) a handle bar of a handglider.

9. A method for providing biofeedback to a user regarding one or more movements executed by the user, the method comprising the steps of:
providing a movement assessment apparatus configured to be worn by a user, the movement assessment apparatus including:
at least one sensing device, the at least one sensing device comprising one or more sensors for detecting the motion of a body portion of a user and/or the motion of an object manipulated by the user and outputting one or more signals that are generated based upon the motion of the body portion of the user and/or the motion of the object, the at least one sensing device further comprising attachment means for attaching the at least one sensing device to the body portion of the user or to the object manipulated by the user;

a data processing device operatively coupled to the at least one sensing device, the data processing device configured to receive the one or more signals that are output by the one or more sensors of the at least one sensing device, and to determine executed motion data of the body portion of the user or executed motion data of the object manipulated by the user using the one or more signals, the data processing device further configured to: (i) execute an agreement operation by converting the executed motion data to a feedback-agreeing form that agrees with at least one of the dimensions, reference frames, and units of baseline motion data of a reference motion, (ii) execute a comparison operation by comparing the feedback-agreeing form of the executed motion data to the baseline motion data of the reference motion, and (iii) determine how closely the feedback-agreeing form of the executed motion data conforms to the baseline motion data of the reference motion, the data processing device additionally configured to generate an abstract feedback signal based upon the execution of the comparison operation; and a sensory output device operatively coupled to the data processing device, the sensory output device configured to generate a formed feedback signal for delivery to the user that is based upon the abstract feedback signal, the formed feedback signal comprising at least one of a visual indicator, an audible indicator, and a tactile indicator, and the sensory output device further configured to output the at least one of the visual indicator, the audible indicator, and the tactile indicator to the user in order to provide biofeedback as to conformity of the executed motion data to the baseline motion data of the reference motion;

outfitting a user or an object with the movement assessment apparatus, which includes attaching the attachment means of the at least one sensing device to a body portion of the user or to the object manipulated by the user;

instructing the user to perform an activity where the user displaces at least one of the body portion of the user and/or the object manipulated by the user;

detecting, by utilizing the at least one sensing device, the motion of the body portion of the user and/or the motion of the object manipulated by the user, and outputting one or more signals that are generated based upon the motion of the body portion of the user and/or the motion of the object manipulated by the user;

receiving, at the data processing device, the one or more signals that are output by the one or more sensors of the at least one sensing device;

determining, by using the data processing device, executed motion data for an executed motion of the body portion of the user and/or for an executed motion of the object manipulated by the user using the one or more signals;

executing an agreement operation, by using the data processing device, whereby the executed motion data is converted to a feedback-agreeing form that agrees with at least one of the dimensions, reference frames, and units of baseline motion data of a reference motion;

executing a comparison operation, by using the data processing device, whereby the feedback-agreeing form of the executed motion data is compared to the baseline motion data of the reference motion;

determining, by using the data processing device, how closely the feedback-agreeing form of the executed motion data conforms to the baseline motion data of the reference motion;

generating, by using the data processing device, an abstract feedback signal based upon the execution of the comparison operation;

generating, by using the sensory output device, a formed feedback signal for delivery to the user that is based upon the abstract feedback signal, the formed feedback signal comprising at least one of a visual indicator, an audible indicator, and a tactile indicator; and outputting the at least one of the visual indicator, the audible indicator, and the tactile indicator from the sensory output device to the user in order to provide quasi-instantaneous, real-time biofeedback as to conformity of the executed motion data to the baseline motion data of the reference motion.

10. A movement assessment apparatus configured to provide biofeedback to a user regarding one or more movements executed by the user, the movement assessment apparatus comprising:

at least one sensing device, the at least one sensing device comprising one or more sensors for detecting the motion of a body portion of a user and/or the motion of an object manipulated by the user and outputting one or more signals that are generated based upon the motion of the body portion of the user and/or the motion of the object, the at least one sensing device further comprising attachment means for attaching the at least one sensing device to the body portion of the user or to the object manipulated by the user;

at least one input device, the at least one input device configured to enable the user to manually select an activity from a plurality of activities, the selected activity having one or more reference motions associated therewith;

a data processing device operatively coupled to the at least one sensing device and the at least one input device, the data processing device configured to receive the one or more signals that are output by the one or more sensors of the at least one sensing device, and to determine executed motion data of the body portion of the user and/or executed motion data of the object manipulated by the user using the one or more signals, the data processing device further configured to: (i) execute an agreement operation by converting the executed motion data to a feedback-agreeing form that agrees with at least one of the dimensions, reference frames, and units of baseline motion data of the one or more reference motions, (ii) execute a comparison operation by comparing the feedback-agreeing form of the executed motion data to the baseline motion data of the one or more reference motions, and (iii) determine how closely the feedback-agreeing form of the executed motion data conforms to the baseline motion data of the one or more reference motions, the data processing device additionally configured to generate an abstract feedback signal based upon the execution of the comparison operation; and a sensory output device operatively coupled to the data processing device, the sensory output device configured to generate a formed feedback signal for delivery to the user that is based upon the abstract feedback signal, the formed feedback signal comprising at least one of a visual indicator, an audible indicator, and a tactile indicator, and the sensory output device further configured to output the at least one of the visual indicator, the audible indicator, and the tactile indicator to the user in order to provide biofeedback as to conformity of the executed motion data to the baseline motion data of the one or more reference motions.

11. The movement assessment apparatus according to claim 10, wherein the at least one input device comprises a user interface disposed on a housing containing at least one of the at least one sensing device and the data processing device.

12. The movement assessment apparatus according to claim 11, wherein the user interface comprises at least one of: (i) one or more selection buttons or knobs, (ii) a keypad or keyboard, and (iii) a touchscreen-type visual display device.

13. The movement assessment apparatus according to claim 10, wherein the one or more sensors of the at least one sensing device are configured to detect the motion of an object manipulated by the user, wherein the at least one input device comprises a user interface disposed on the object, and wherein the object comprises a sports implement.

14. The movement assessment apparatus according to claim 13, wherein the sports implement comprises one of: (i) a golf club, (ii) a baseball bat or softball bat, (iii) a tennis racket, (iv) an oar for rowing a boat, (v) a ski, and (vi) a ski pole.

15. The movement assessment apparatus according to claim 10, wherein the sensory output device comprises an auditory sensory output device configured to generate the audible indicator that provides biofeedback as to the conformity of the executed motion data to the baseline motion data of the one or more reference motions.

16. The movement assessment apparatus according to claim 10, wherein the sensory output device comprises a light emitting device configured to be worn by the user, and wherein the light emitting device is configured to generate the visual indicator that provides biofeedback as to the conformity of the executed motion data to the baseline motion data of the one or more reference motions.

17. The movement assessment apparatus according to claim 10, wherein the sensory output device comprises a vibratory device configured to be worn by the user, and wherein the vibratory device is configured to generate the tactile indicator that provides biofeedback as to the conformity of the executed motion data to the baseline motion data of the one or more reference motions.

18. The movement assessment apparatus according to claim 10, wherein the one or more sensors of the at least one sensing device are configured to detect the motion of an object manipulated by the user, and wherein the object manipulated by the user comprises one of: (i) a golf club, (ii) a baseball bat or softball bat, (iii) a tennis racket, (iv) an oar for rowing a boat, (v) a ski, (vi) a ski pole, and (vii) a handle bar of a handglider.

* * * * *